United States Patent
Lan

(10) Patent No.: US 10,184,080 B2
(45) Date of Patent: Jan. 22, 2019

(54) LIQUID CRYSTAL MATERIALS, METHODS OF FABRICATING LIQUID CRYSTAL DISPLAY PANELS AND LIQUID CRYSTAL DISPLAY PANELS

(71) Applicant: Shenzhen China Star Optoelectronics Technology Co., Ltd., Shenzhen (CN)

(72) Inventor: Song Lan, Shenzhen (CN)

(73) Assignee: SHENZHEN CHINA STAR OPTOELECTRONICS TECHNOLOGY CO., LTD., Shenzhen, Guangdong (CN)

( * ) Notice: Subject to any disclaimer, the term of this patent is extended or adjusted under 35 U.S.C. 154(b) by 254 days.

(21) Appl. No.: 15/106,839

(22) PCT Filed: May 18, 2016

(86) PCT No.: PCT/CN2016/082556
§ 371 (c)(1),
(2) Date: Jun. 21, 2016

(87) PCT Pub. No.: WO2017/181466
PCT Pub. Date: Oct. 26, 2017

(65) Prior Publication Data
US 2018/0105750 A1    Apr. 19, 2018

(30) Foreign Application Priority Data
Apr. 22, 2016 (CN) .......................... 2016 1 0257619

(51) Int. Cl.
| | | |
|---|---|---|
| *G02F 1/1333* | (2006.01) | |
| *C09K 19/56* | (2006.01) | |
| *C07C 69/65* | (2006.01) | |
| *G02F 1/1337* | (2006.01) | |
| *G02F 1/1343* | (2006.01) | |
| *G02F 1/1368* | (2006.01) | |

(52) U.S. Cl.
CPC .............. *C09K 19/56* (2013.01); *C07C 69/65* (2013.01); *G02F 1/133711* (2013.01); *G02F 1/134309* (2013.01); *G02F 1/1368* (2013.01); *G02F 2001/133742* (2013.01); *G02F 2001/133776* (2013.01); *G02F 2201/121* (2013.01); *G02F 2201/123* (2013.01); *G02F 2202/022* (2013.01)

(58) Field of Classification Search
CPC ....... C09K 19/56; C07C 69/65; G02F 1/1368; G02F 1/134309; G02F 1/133711; G02F 2202/022; G02F 2001/133742; G02F 2001/133776; G02F 2201/121; G02F 2201/123
USPC ................................................... 252/299.01
See application file for complete search history.

(56) References Cited

FOREIGN PATENT DOCUMENTS

CN        105001879 A    10/2015

*Primary Examiner* — Geraldina Visconti
(74) *Attorney, Agent, or Firm* — Leong C. Lei

(57) ABSTRACT

The present application provides a liquid crystal material, a method of fabricating a liquid crystal display panel, and a liquid crystal display panel. The liquid crystal material of the present application includes liquid crystal molecules, polymerizable monomers and a reactive vertical alignment material, the polymerizable monomers and the reactive vertical alignment material can occur a polymerization under ultraviolet irradiation to form a polymer, while the polymer deposits on a substrate to form a polymer film capable of replacing the PI alignment film, the reactive vertical alignment material includes a polymerizable group L that strengthens polymerization ability of the reactive vertical alignment material, increases compactness of forming the polymer film, improves morphology of the polymer film, and enhances panel quality. The method of fabricating the liquid crystal display panel of the present application eliminates the fabricating process of the PI alignment film, the method has simple process and low cost. The liquid crystal display panel utilizes the polymer film, which is obtained by polymerizing the polymerizable monomers and the reactive vertical alignment material, to replace the PI alignment film, so as to greatly enhance quality of the panel, and to have a low fabricating cost.

7 Claims, 5 Drawing Sheets

US 10,184,080 B2

LIQUID CRYSTAL MATERIALS, METHODS OF FABRICATING LIQUID CRYSTAL DISPLAY PANELS AND LIQUID CRYSTAL DISPLAY PANELS

FIELD OF THE INVENTION

The present application relates to display technology field, especially to a liquid crystal material, a method of fabricating a liquid crystal display panel, and a liquid crystal display panel.

BACKGROUND OF THE INVENTION

With the development of the display technology, due that flat display devices of liquid crystal displays (LCD) and the like have advantages of high definition, power saving, thin body, wide range application etc., the flat display devices are widely applied to various consumer electronic products of mobile phones, televisions, personal digital assistants, notebook computers, desktop computers and the like, so as to be the mainstream of the display devices.

Most of the liquid crystal devices in current market are backlight type liquid crystal display, which includes a liquid crystal display panel and a backlight module. The working principle of the liquid crystal display panel is: placing liquid crystal molecules in two parallel glass substrates, which have many vertical and horizontal fine wires between the two glass substrates; controlling the liquid crystal molecules to change direction by energizing or not energizing; and refracting light of the backlight module to produce frames.

Generally, the liquid crystal display panel is consisting of a color filter (CF) substrate, a thin film transistor (TFT) substrate, liquid crystal interposed between the CF substrate and the TFT substrate, and a sealant.

A thin film material is respectively formed on the CF substrate and the TFT substrate in the liquid crystal display, a main action of the thin film material is to arrange for the liquid crystal molecules according to a certain direction, the thin film material, we call an alignment film, usually is polyimide (PI) material. A main composition of this type alignment film is a rubbing alignment type PI material or an optical alignment type PI material; however, no matter what the type of alignment material is, it has its own shortcoming. Firstly, the rubbing alignment type PI material easily causes problems of dust particles, residual electrostatic, and brush mark etc.; thereby reducing process yield. Although the optical alignment PI material can obviate such problems, it has limited material characteristics, poor heat resistance, poor aging resistance, and weaker ability of anchoring liquid crystal molecules; thereby affecting panel quality. Secondly, the PI material itself has high polarity and high water absorption, storage and transport easily cause deterioration that results in uneven alignment, and the price of PI material is expensive, the process of forming a film on the TFT-LCD is complex; thereby increasing panel cost.

Additionally, the PI solution, used in fabricating the alignment film, contains a large amount of solvent N-methylpyrrolidone (NMP); therefore, the process of forming the alignment film is a high energy consuming, not environmentally friendly and human harmful process; moreover, due to the alignment film having issues of evenness, lack of coating, non-stick and foreign matter, the use of alignment film will result in product yield loss, resource waste, and product cost elevation. In the fabrication of liquid crystal display panel, if the arrangement of liquid crystal molecules is made by omitting the PI film, the cost of fabricating panels will be greatly reduced.

SUMMARY OF THE INVENTION

A primary aspect of the present application is to provide a liquid crystal material, including liquid crystal molecules, a reactive vertical alignment material, and polymerizable monomers, the polymerizable monomers can occur a polymerization with the reactive vertical alignment material to form a polymer, the polymer deposits on a substrate to form a polymer film, which can replace the PI alignment film, so that an alignment process of liquid crystal is simplified, a cost is economized.

Another aspect of the present application is to provide a method of fabricating a liquid crystal display panel. The method eliminates a fabricating process of the PI alignment film, has simple process and low cost.

A further aspect of the present application is to provide a liquid crystal display panel utilizing a polymer film, which is obtained by polymerizing the polymerizable monomers and the reactive vertical alignment material, to replace the PI alignment film, that not only meets the aspect of liquid crystal alignment, but also prevent impurities in the CF substrate to diffuse into the liquid crystal layer, so as to greatly enhance quality of the panel, and to have a low fabricating cost.

To achieve the aforesaid aspects, the present application provides a liquid crystal material, including liquid crystal molecules, a reactive vertical alignment material, and polymerizable monomers;

a structural formula of the reactive vertical alignment material being

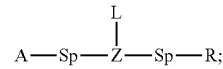

wherein A refers —OH, —COOH, —NH$_2$, or —NH—;
Sp refers group —(CH$_2$)$_n$—, or a group obtained by a —CH$_2$— in the group —(CH$_2$)$_n$— substituted with —O—, —S—, —CO—, —CO—O—, —O—CO—, —O—CO—O—, —OCH$_2$—, —CH$_2$O—, —CH=CH—, —CF=CF—, —C≡C—, —CH=CH—COO—, or —OCO—CH=CH—, wherein n is an integer 1~8;
Z refers

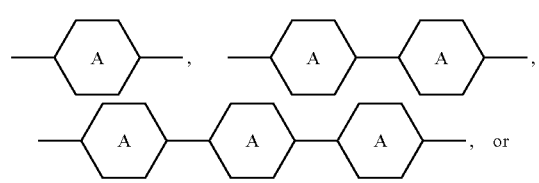

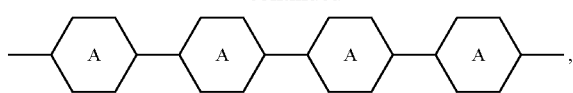

wherein

is phenyl, a group obtained by an H atom in phenyl substituted with F, Cl, Br, I, —CN, —NO$_2$, or —C(=O)H, or cycloalkyl; R refers alkyl of straight chain or branched chain having 5~20 C atoms, a first group obtained by a —CH$_2$— in the alkyl substituted with phenyl, cycloalkyl, —CONH—, —COO—, —O—CO—, —S—, —CO—, or —CH=CH—, a second group obtained by an H atom in the alkyl substituted with F or Cl atom, or a third group obtained by an H atom in the first group substituted with F or Cl atom;

L refers a polymerizable group connecting to group Z, and includes any one, any two, or any three of following three groups:

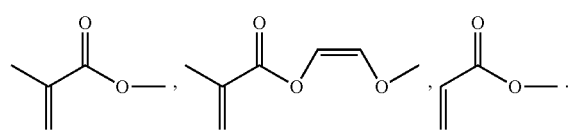

The reactive vertical alignment material includes one or more than one of following compounds:

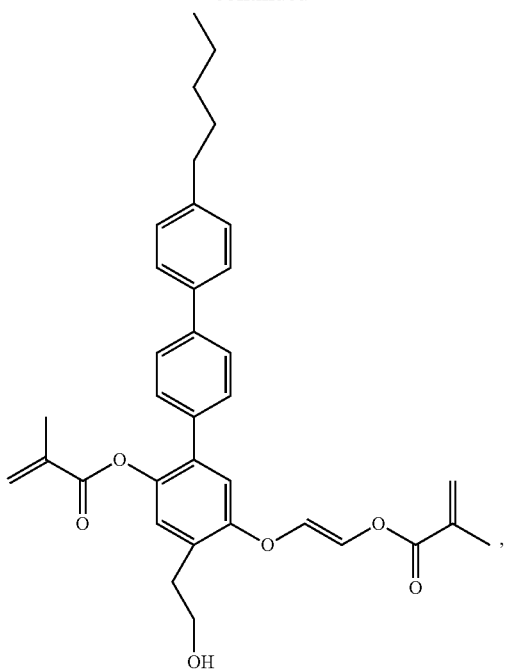

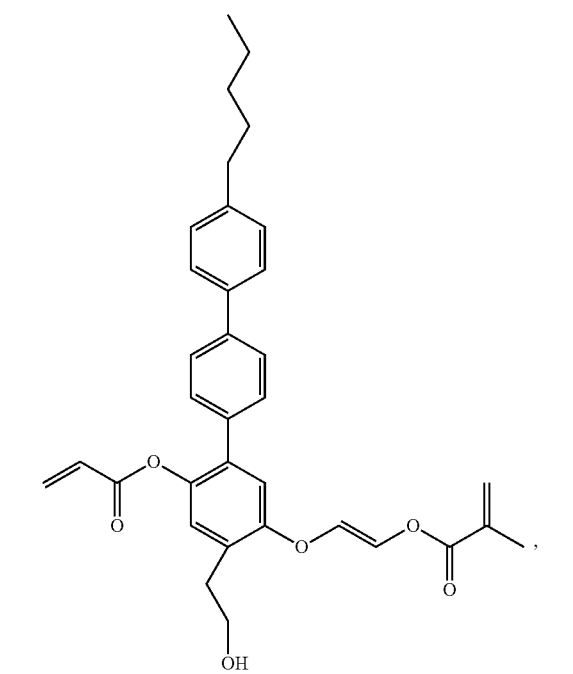

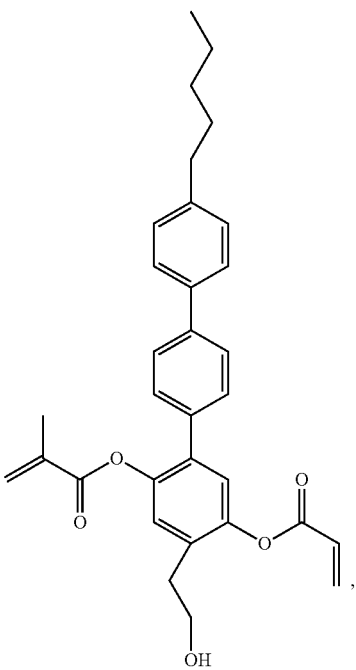

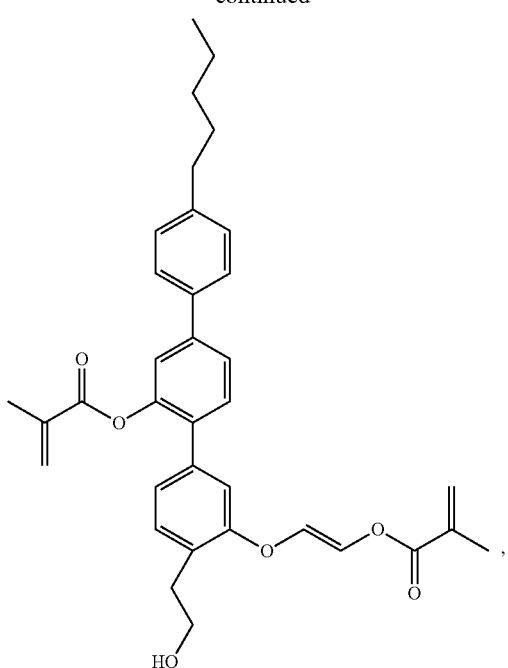

,

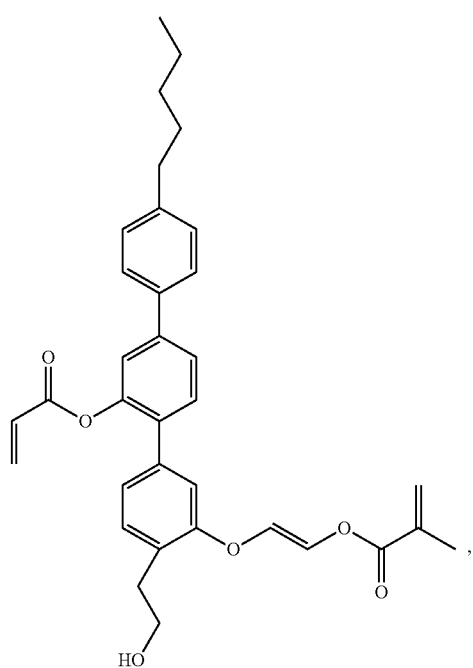

,

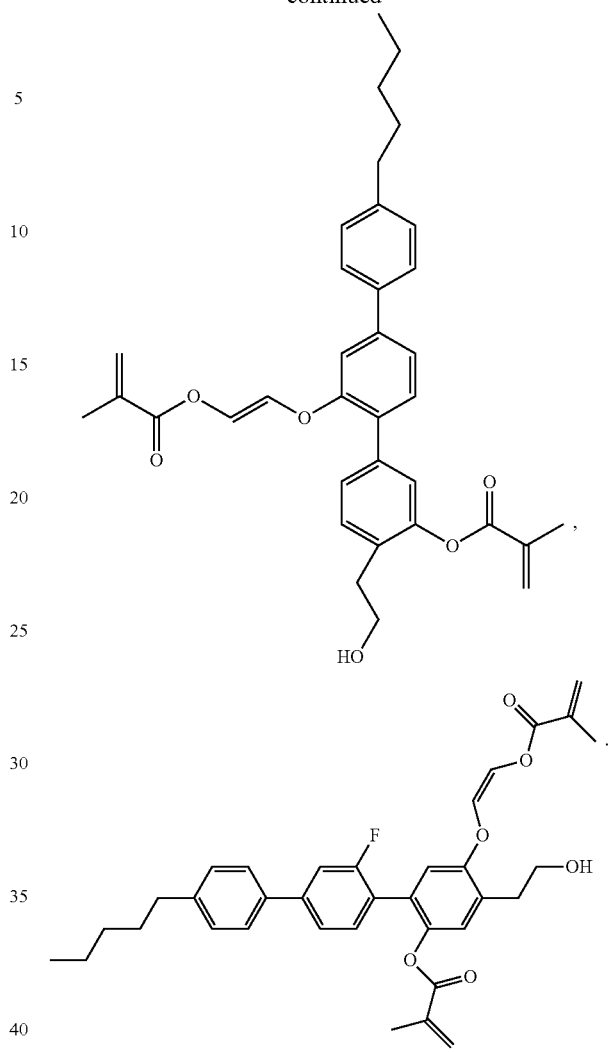

A mass percentage of the liquid crystal molecules is 93.0%~99.4%, a mass percentage of the reactive vertical alignment material is 0.5%~5.0%, a mass percentage of the polymerizable monomers is 0.01%~02.0%.

The polymerizable monomers include one or a combination of more than one of acrylates, acrylate derivatives, methacrylates, methacrylate derivatives, styrene, styrene derivatives, and epoxy resin.

The present application further provides a method of fabricating a liquid crystal display panel, including following steps:

step 1, providing an upper substrate, a lower substrate, and a liquid crystal material;

the upper substrate including a first substrate, and a first electrode disposed on the first substrate; the lower substrate including a second substrate, and a second electrode disposed on the second substrate;

the liquid crystal material including liquid crystal molecules, a reactive vertical alignment material, and polymerizable monomers;

a structural formula of the reactive vertical alignment material being

wherein A refers —OH, —COOH, —NH$_2$, or —NH—;

Sp refers group —(CH$_2$)$_n$—, or a group obtained by a —CH$_2$— in the group —(CH$_2$)$_n$— substituted with —O—, —S—, —CO—, —CO—O—, —O—CO—, —O—CO—O—, —OCH$_2$—, —CH$_2$O—, —CH═CH—, —CF═CF—, —C≡C—, —CH═CH—COO—, or —OCO—CH═CH—, wherein n is an integer 1~8;

Z refers

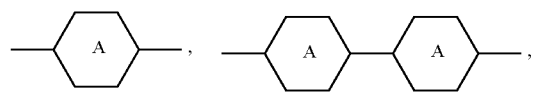

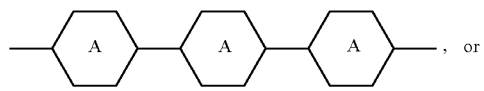

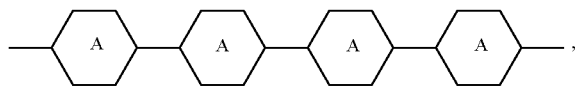

wherein

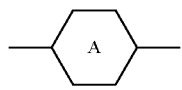

is phenyl, a group obtained by an H atom in phenyl substituted with F, Cl, Br, I, —CN, —NO$_2$, or —C(═O)H, or cycloalkyl;

R refers alkyl of straight chain or branched chain having 5~20 C atoms, a first group obtained by a —CH$_2$— in the alkyl substituted with phenyl, cycloalkyl, —CONH—, —COO—, —O—CO—, —S—, —CO—, or —CH═CH—, a second group obtained by an H atom in the alkyl substituted with F or Cl atom, or a third group obtained by an H atom in the first group substituted with F or Cl atom;

L refers a polymerizable group connecting to group Z, and includes any one, an two, or any three of following three groups:

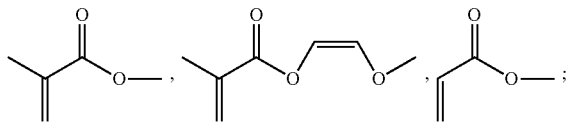

step 2, dripping the liquid crystal material on the upper substrate or the lower substrate, coating a sealant on a peripheral position of the upper substrate or the lower substrate, then assembling and laminating the upper substrate and the lower substrate, and curing the sealant;

the reactive vertical alignment material in the liquid crystal material adsorbs the upper substrate and the lower substrate, and arranges perpendicular to the upper substrate and the lower substrate, so as to guide the liquid crystal molecules arranging perpendicular to the upper substrate and the lower substrate;

step 3, applying a voltage to both sides of the liquid crystal material through the first electrode and the second electrode, to allow the liquid crystal molecules occurring deflection and arranging along a direction inclined to the upper substrate and the lower substrate;

step 4, under the condition of applying the voltage to the liquid crystal material, irradiating ultraviolet to the liquid crystal material from a side of the upper substrate or the lower substrate, to allow the reactive vertical alignment material in the liquid crystal material occurring a polymerization with the polymerizable monomer to form a polymer, wherein the polymer deposits on the upper substrate toward a side of the liquid crystal material to form a first polymer film, and simultaneously deposits on the lower substrate toward a side of the liquid crystal material to form a second polymer film, surfaces of both the first polymer film and the second polymer film have polymer projections, so as to allow the liquid crystal molecules near the first polymer film and the second polymer film maintain the inclined direction thereof in a steric hindrance manner, after the voltage is removed;

constituting a liquid crystal layer by the liquid crystal material in which the reactive vertical alignment material and of polymerizable monomers are removed, to complete the fabrication of the liquid crystal display panel.

The reactive vertical alignment material includes one or more than one of following compounds:

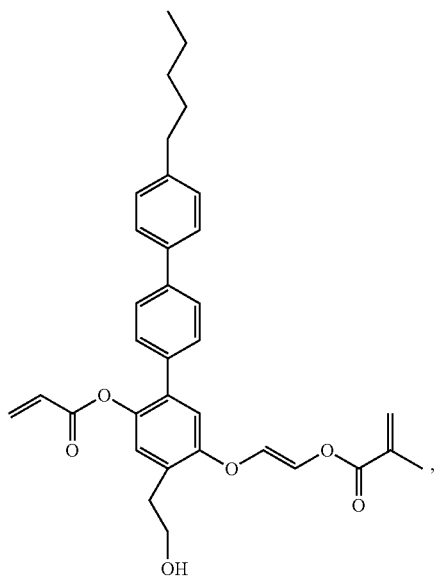

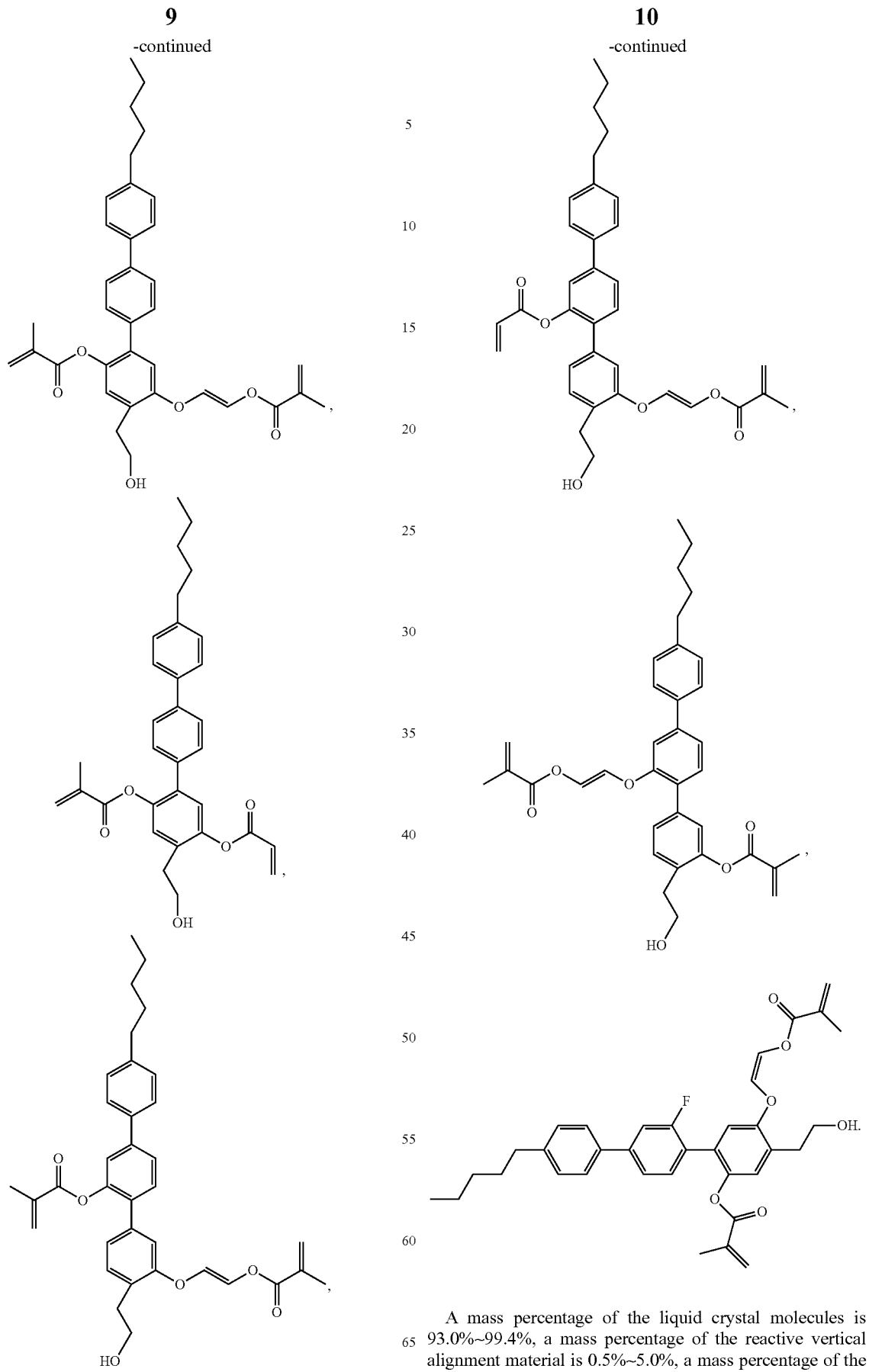
A mass percentage of the liquid crystal molecules is 93.0%~99.4%, a mass percentage of the reactive vertical alignment material is 0.5%~5.0%, a mass percentage of the polymerizable monomers is 0.01%~2.0%.

The polymerizable monomers include one or a combination of more than one of acrylates, acrylate derivatives, methacrylates, methacrylate derivatives, styrene, styrene derivatives, and epoxy resin.

In step 3, the voltage applied to the both sides of the liquid crystal material is 13~25V; in the irradiating ultraviolet of step 4, an illumination intensity of the ultraviolet is 85~100 mW/cm$^2$, an irradiation time is 20~30 min, thicknesses of the first polymer film and the second polymer film are 100~1200 Å.

The present application further provides a liquid crystal display panel, including: oppositely disposed an upper substrate and a lower substrate, a liquid crystal layer disposed between the upper substrate and the lower substrate, a first polymer film disposed on the upper substrate toward a side surface of the liquid crystal layer, and a second polymer film disposed on the lower substrate toward a side surface of the liquid crystal layer; wherein the upper substrate includes a first substrate and a first electrode disposed on the first substrate; the lower substrate includes a second substrate and a second electrode disposed on the second substrate;

the liquid crystal layer includes liquid crystal molecules;

both the first polymer film and the second polymer film are formed by polymerizing the polymerizable monomer and the reactive vertical alignment material, and surfaces of both the first polymer film and the second polymer film have polymer projections, so as to allow the liquid crystal molecules near the first polymer film and the second polymer film arrange along a direction inclined to the upper substrate and the lower substrate;

a structural formula of the reactive vertical alignment material is

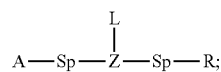

wherein A refers —OH, —COOH, —NH$_2$, or —NH—;
Sp refers group —(CH$_2$)$_n$—, or a group obtained by a —CH$_2$— in the group —(CH$_2$)$_n$— substituted with —O—, —S—, —CO—, —CO—O—, —O—CO—, —O—CO—O—, —OCH$_2$—, —CH$_2$O—, —CH=CH—, —CF=CF—, —C≡C—, —CH=CH—COO—, or —OCO—CH=CH—, wherein n is an integer 1~8;
Z refers

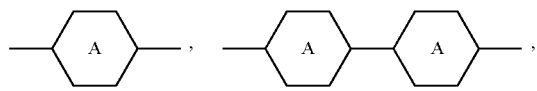

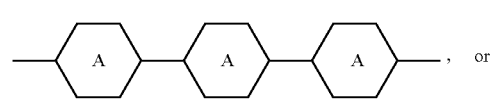

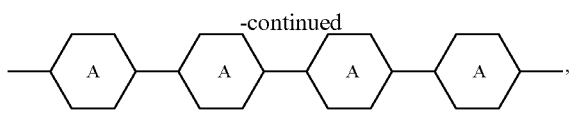

wherein

is phenyl, a group obtained by an H atom in phenyl substituted with F, Cl, Br, I, —CN, —NO$_2$, or —C(=O)H, or cycloalkyl;

R refers alkyl of straight chain or branched chain having 5~20 C atoms, a first group obtained by a —CH$_2$— in the alkyl substituted with phenyl, cycloalkyl, —CONH—, —COO—, —O—CO—, —S—, —CO—, or —CH=CH—, a second group obtained by an H atom in the alkyl substituted with F or Cl atom, or a third group obtained by an H atom in the first group substituted with F or Cl atom;

L refers a polymerizable group connecting to group Z, and includes any one, any two, or any three of following three groups:

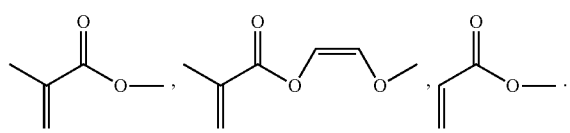

The reactive vertical alignment material includes one or more than one of following compounds:

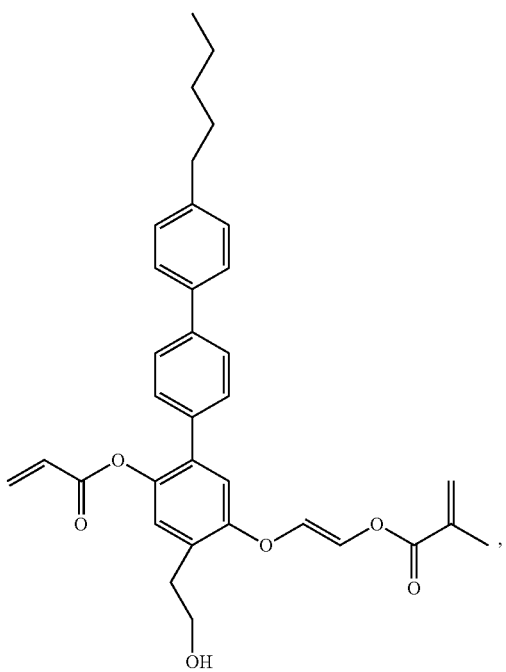

13
-continued
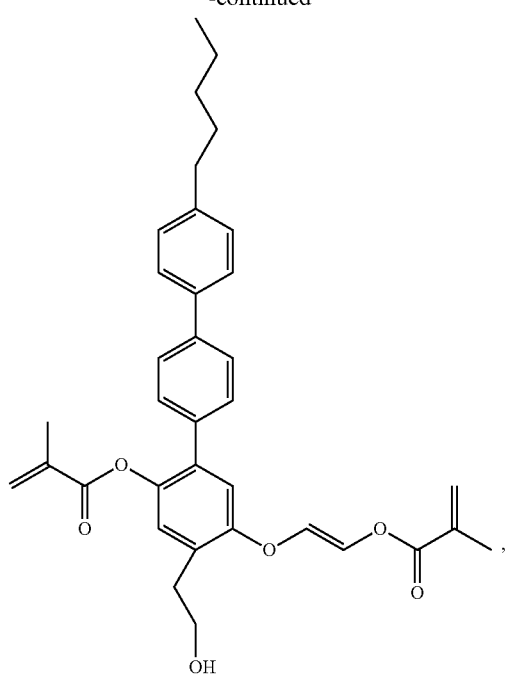
14
-continued
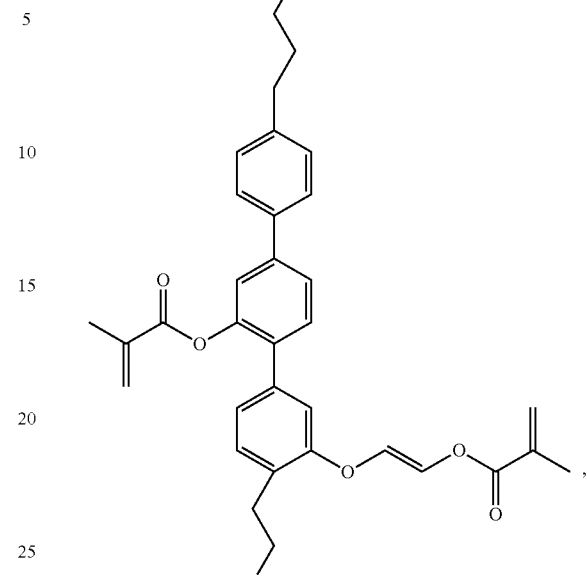
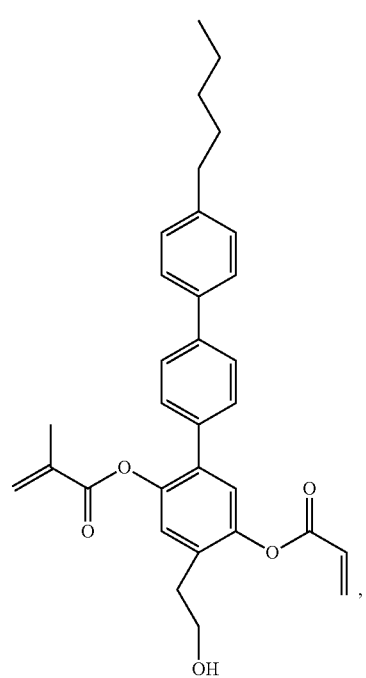
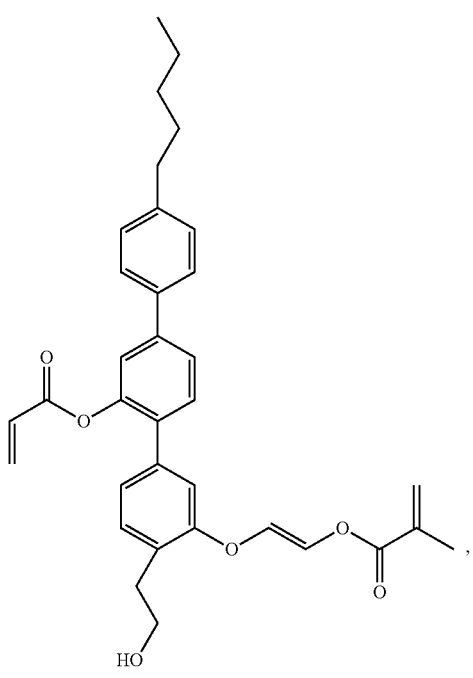

-continued

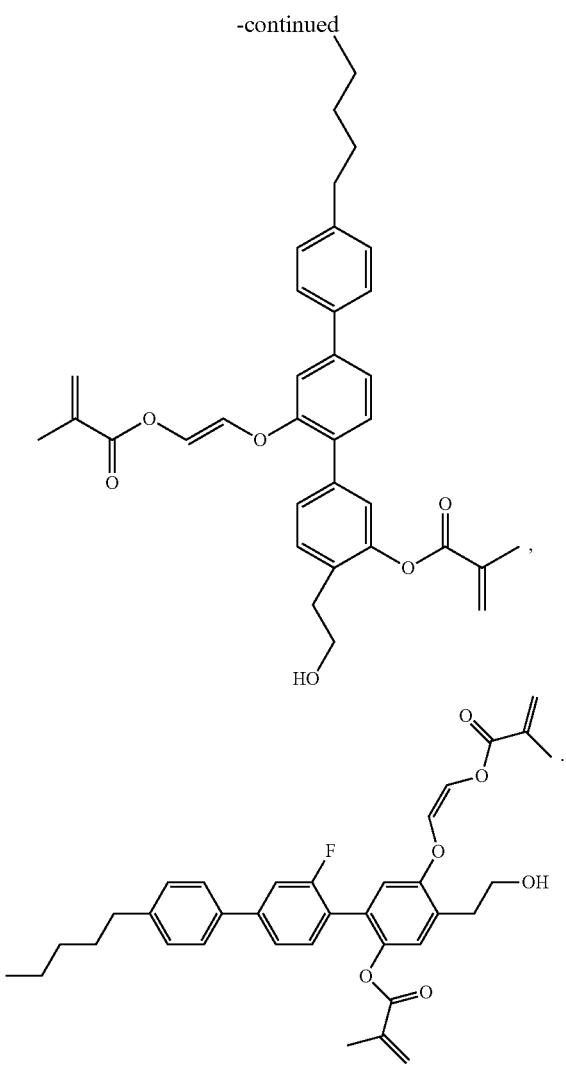

The polymerizable monomers include one or a combination of more than one of acrylates, acrylate derivatives, methacrylates, methacrylate derivatives, styrene, styrene derivatives, and epoxy resin; thicknesses of the first polymer film and the second polymer film are 100~1200 Å.

Advantages of the present application: the liquid crystal material of the present application includes liquid crystal molecules, polymerizable monomers and a reactive vertical alignment material, the polymerizable monomers and the reactive vertical alignment material can occur a polymerization under ultraviolet irradiation to form a polymer, while the polymer deposits on a substrate to form a polymer film capable of replacing the PI alignment film, the reactive vertical alignment material includes a polymerizable group L that strengthens polymerization ability of the reactive vertical alignment material, increases compactness of forming the polymer film, improves morphology of the polymer film, and enhances panel quality. The method of fabricating the liquid crystal display panel of the present application eliminates the fabricating process of the PI alignment film, the method has simple process and low cost. The liquid crystal display panel utilizes the polymer film, which is obtained by polymerizing the polymerizable monomers and the reactive vertical alignment material, to replace the PI alignment film, that not only meets the aspect of liquid crystal alignment, but also prevent impurities in the CF substrate to diffuse into the liquid crystal layer, so as to greatly enhance quality of the panel, and to have a low fabricating cost.

In order to further understand the technical features and contents of the present application, please refer to the following detailed description and accompanying drawings related to the present application; however, the accompanying drawings are provided only for reference and description, and are not used to limit the present application.

BRIEF DESCRIPTION OF THE DRAWINGS

The technical features and other advantages of the present application will become more readily apparent to those ordinarily skilled in the art, by referring the following detailed description of embodiments of the present application in conjunction with the accompanying drawings.

In the accompanying drawings.

DETAILED DESCRIPTION OF PREFERRED EMBODIMENTS

In order to further clarify the technical means adopted in the present application and the effects thereof, the preferable embodiments of the present application and the accompanying drawings thereof will be more specifically described as follows.

Figure 2:
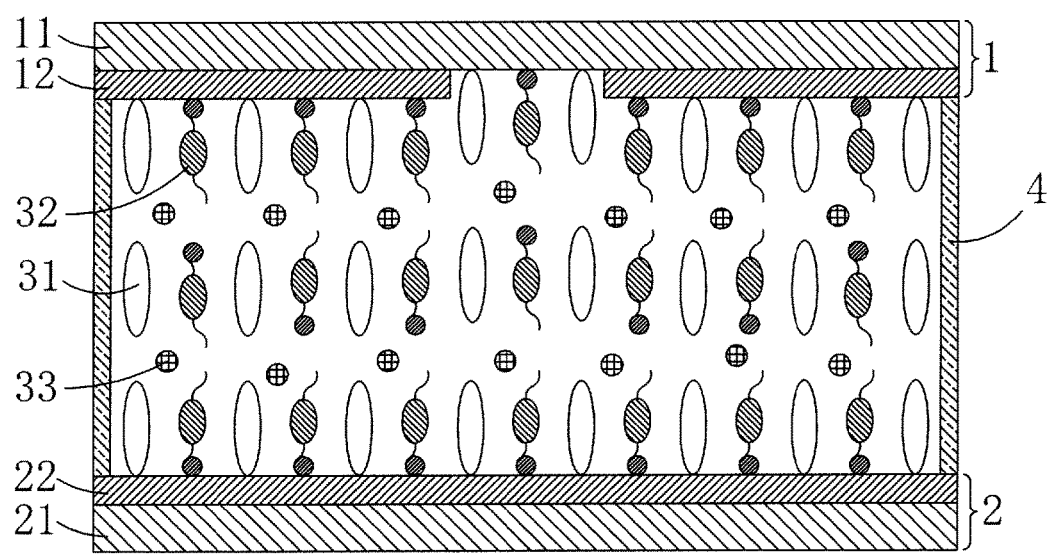
FIG. 2 is a figure schematically illustrating step 1-2 of the method of fabricating the liquid crystal display panel of the present application.

Please refer to FIG. 2, the present application provides a liquid crystal material, including liquid crystal molecules 31, a reactive vertical alignment material 32, and polymerizable monomers (RM) 33.

A structural formula of the reactive vertical alignment material 32 is

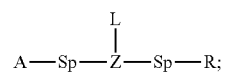

wherein A refers —OH, —COOH, —NH$_2$, or —NH—;

Sp refers group —(CH$_2$)$_n$—, or a group obtained by a —CH$_2$— in the group —(CH$_2$)$_n$— substituted with —O—, —S—, —CO—, —CO—O—, —O—CO—, —O—CO—O—, —OCH$_2$—, —CH$_2$O—, —CH=CH—, —CF=CF—, —C≡C—, —CH=CH—COO—, or —OCO—CH=CH—, wherein n is an integer 1~8;

Z refers

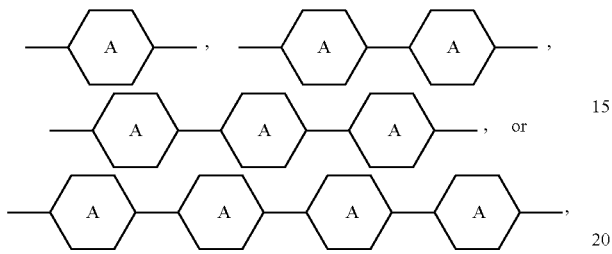

wherein

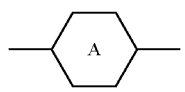

is phenyl, a group obtained by an H atom in phenyl substituted with F, Cl, Br, I, —CN, —NO$_2$, or —C(=O)H, or cycloalkyl;

R refers alkyl of straight chain or branched chain having 5~20 C atoms, a first group obtained by a —CH$_2$— in the alkyl substituted with phenyl, cycloalkyl, —CONH—, —COO—, —O—CO—, —S—, —CO—, or —CH=CH—, a second group obtained by an H atom in the alkyl substituted with F or Cl atom, or a third group obtained by an H atom in the first group substituted with F or Cl atom;

L refers a polymerizable group connecting to group Z, and includes any one, two, or any three of following three groups:

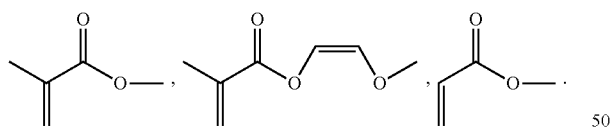

Specifically, in the reactive vertical alignment material 32, the group A is as a head group, which mainly utilizes its polar group to anchor a surface of a inorganic substrate in a physically acting manner; the group Z and the group R play a role similar to a branched chain of PI to allow the liquid crystal molecule be a vertical alignment in a steric hindrance manner; the side chain group L is a polymerizable group containing two or more different types of groups, by adding double bonds, polymerization ability of the reactive vertical alignment material 32 to ultraviolet is strengthened, compactness of forming the polymer film is increased, morphology of the polymer film is improved, and reliability of the panel is enhanced.

Specifically, the reactive vertical alignment material includes one or more than one of following compounds:

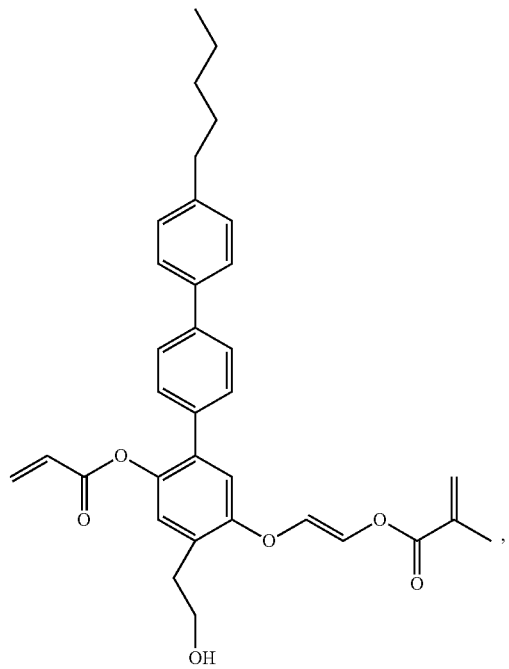

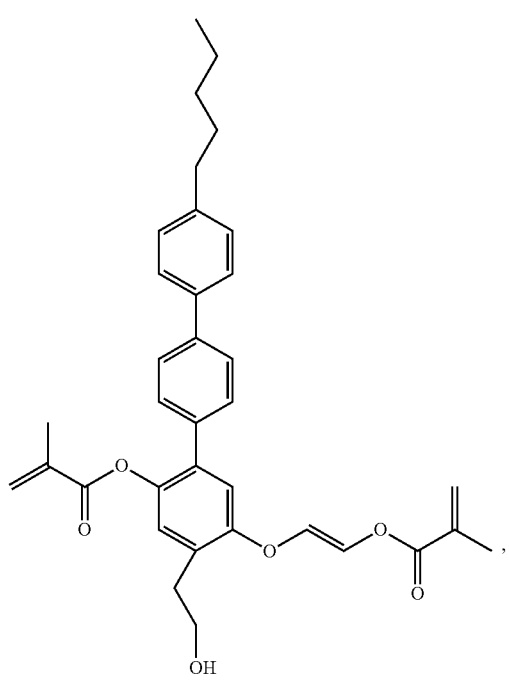

19
-continued
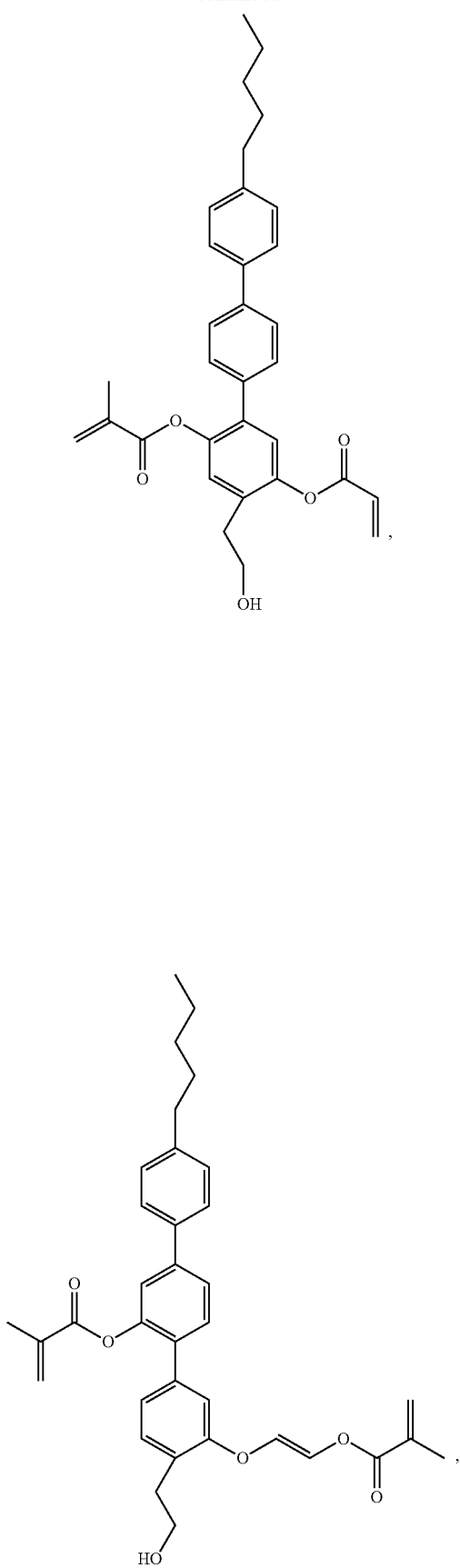
20
-continued
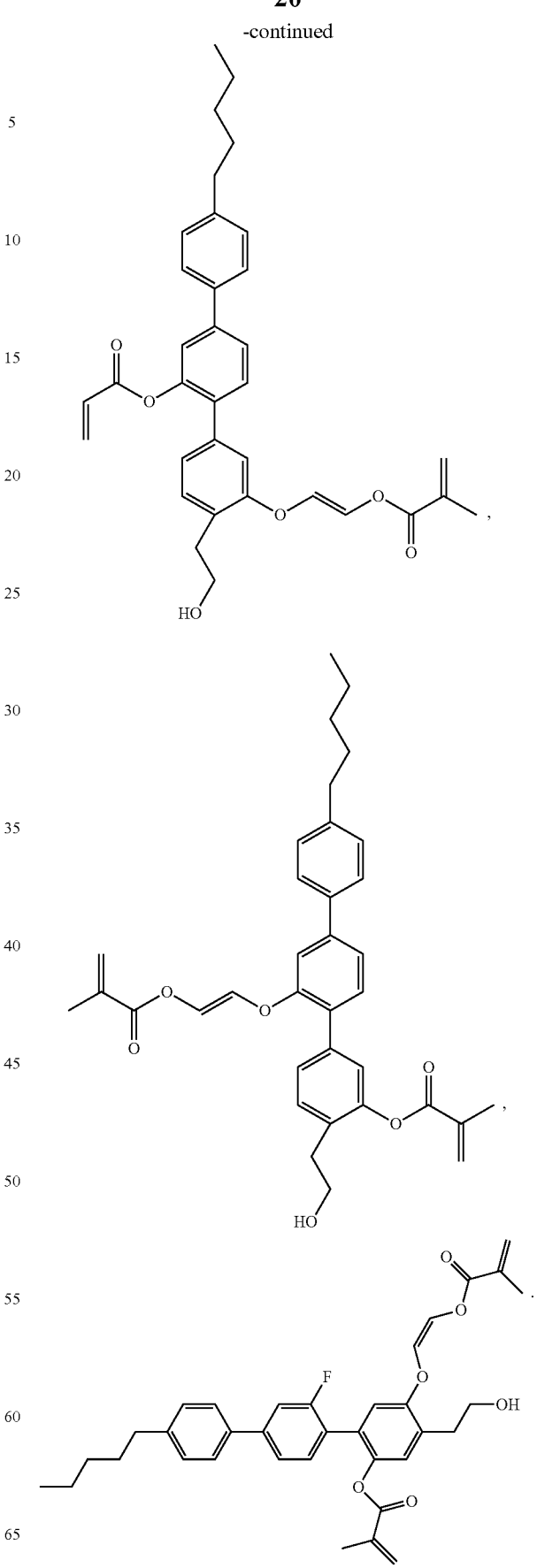

Specifically, in the liquid crystal material, a mass percentage of the liquid crystal molecules 31 is 93.0%~99.4%, a mass percentage of the reactive vertical alignment material 32 is 0.5%~5.0%, a mass percentage of the polymerizable monomers 33 is 0.01%~2.0%.

Specifically, the polymerizable monomers 33 include one or a combination of more than one of acrylates, acrylate derivatives, methacrylates, methacrylate derivatives, styrene, styrene derivatives, and epoxy resin.

Preferably, the liquid crystal material further includes photo initiator, and a mass percentage of the photo initiator is 0.1%~0.5%.

Specifically, the photo initiator includes one or a combination of more than one of azobisisobutyronitrile, dialkyl peroxide base compounds, diacyl peroxide base compounds, and lipid peroxide base compound.

Specifically, the liquid crystal molecules 31 include one or more than one of following compounds:

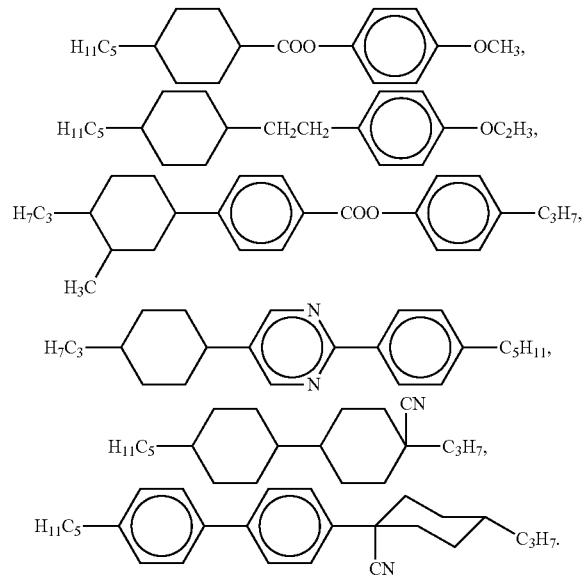

Figure 1:
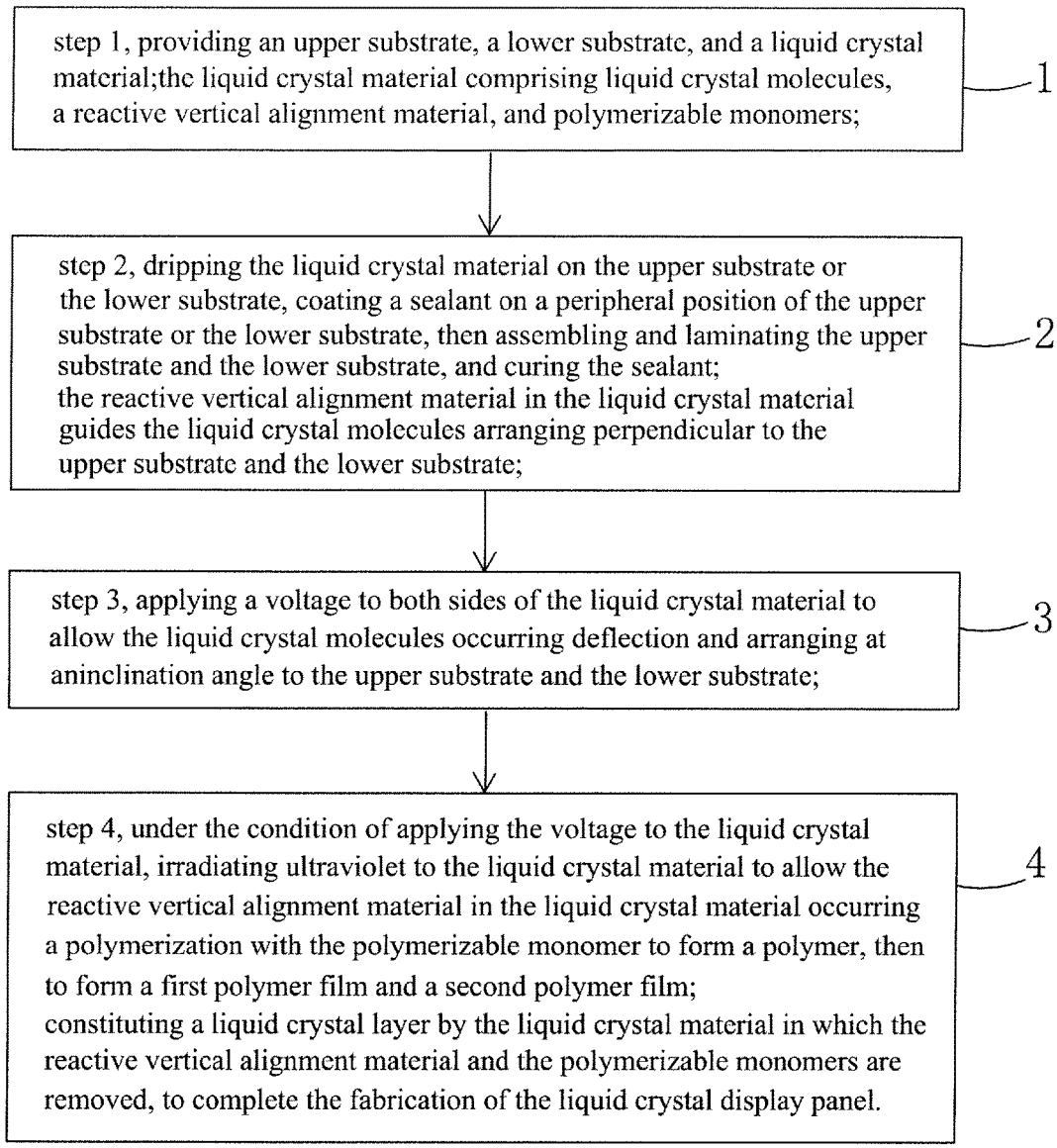
FIG. 1 is a flow chart schematically illustrating a method of fabricating a liquid crystal display panel of the present application.

Please refer to FIG. 1, the present application further provides a method of fabricating a liquid crystal display panel, including following steps.

Step 1, please refer to FIG. 2, providing an upper substrate 1, a lower substrate 2, and a liquid crystal material.

The upper substrate 1 includes a first substrate 11, and a first electrode disposed on the first substrate 11; the lower substrate 2 includes a second substrate 21, and a second electrode 22 disposed on the second substrate 21.

The liquid crystal material includes liquid crystal molecules 31, a reactive vertical alignment material 32, and polymerizable monomers 33.

A structural formula of the reactive vertical alignment material 32 is

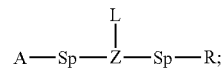

wherein A refers —OH, —COOH, —NH$_2$, or —NH—;

Sp refers group —(CH$_2$)$_n$—, or a group obtained by a —CH$_2$— in the group —(CH$_2$)$_n$— substituted with —O—, —S—, —CO—, —CO—O—, —O—CO—, —O—CO—O—, —OCH$_2$—, —CH$_2$O—, —CH—CH—, —CF=CF—, —C≡C—, —CH—CH—COO—, or —OCO—CH=CH—, wherein n is an integer 1~8;

Z refers

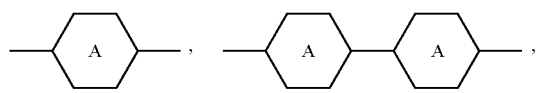

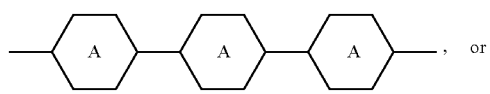

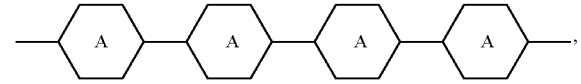

wherein

is phenyl, a group obtained by an H atom in phenyl substituted with F, Cl, Br, I, —CN, —NO$_2$, or —C(=O)H, or cycloalkyl;

R refers alkyl of straight chain or branched chain having 5~20 C atoms, a first group obtained by a —CH$_2$— in the alkyl substituted with phenyl, cycloalkyl, —CONH—, —COO—, —O—CO—, —S—, —CO—, or —CH=CH—, a second group obtained by an H atom in the alkyl substituted with F or Cl atom, or a third group obtained by an H atom in the first group substituted with F or Cl atom;

L refers a polymerizable group connecting to group Z, and includes any one, any two, or any three of following three groups:

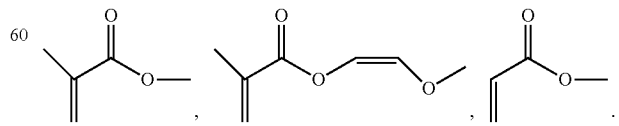

Specifically, the reactive vertical alignment material 32 includes one or more than one of following compounds:

23
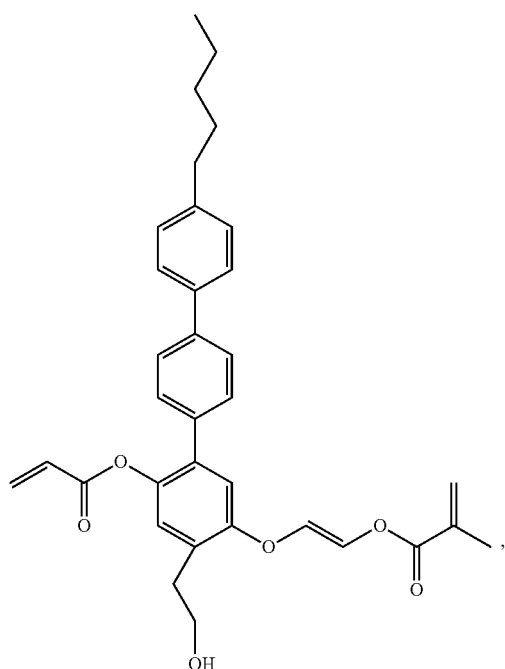
24
-continued
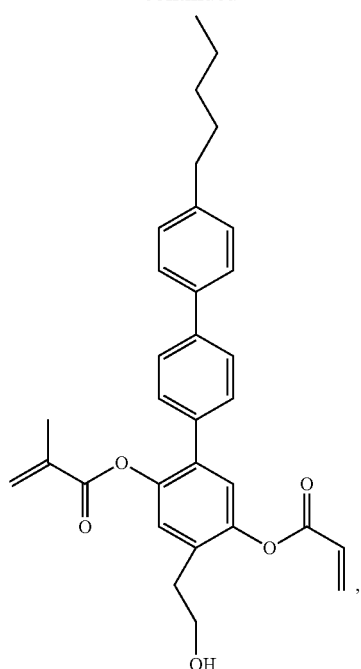
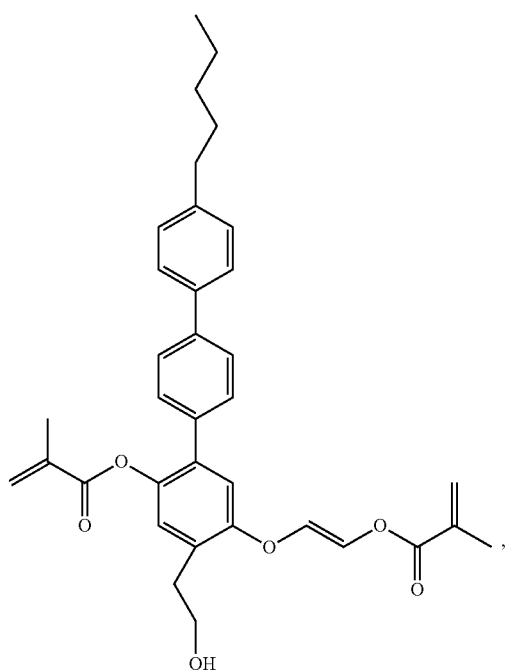
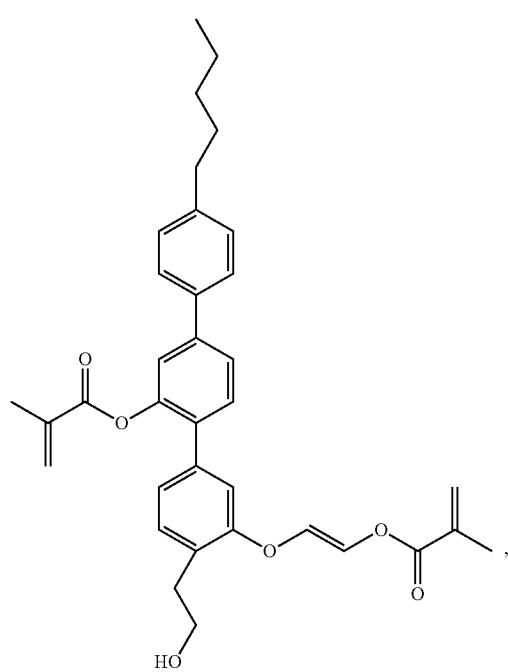

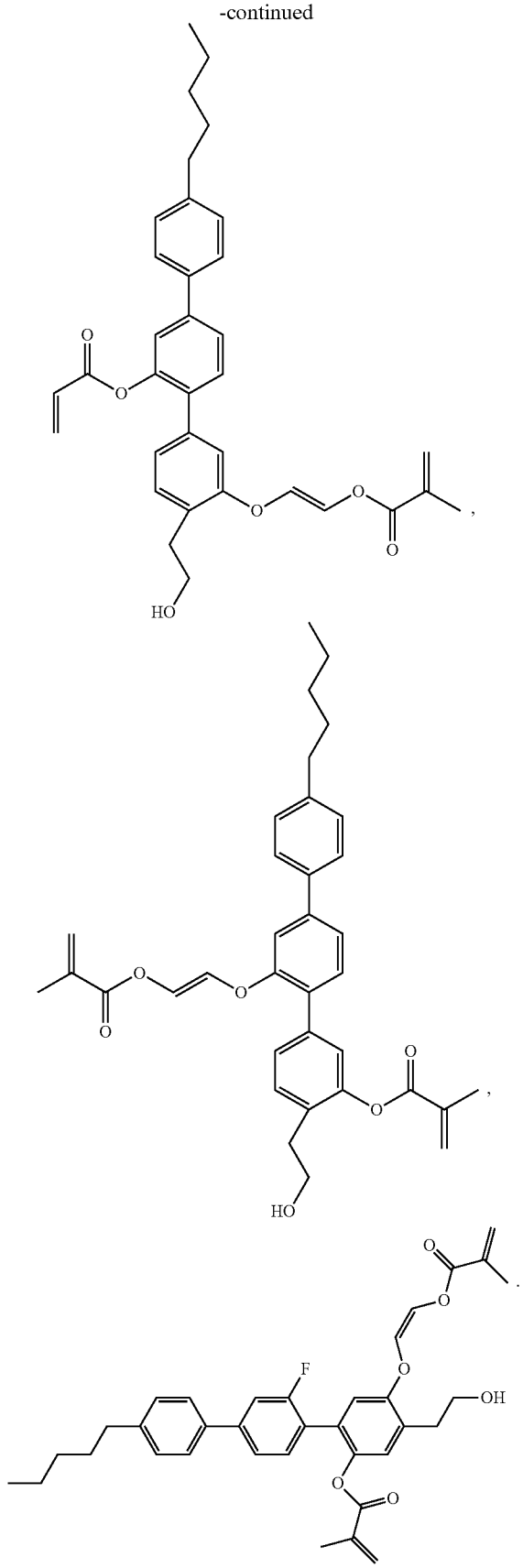

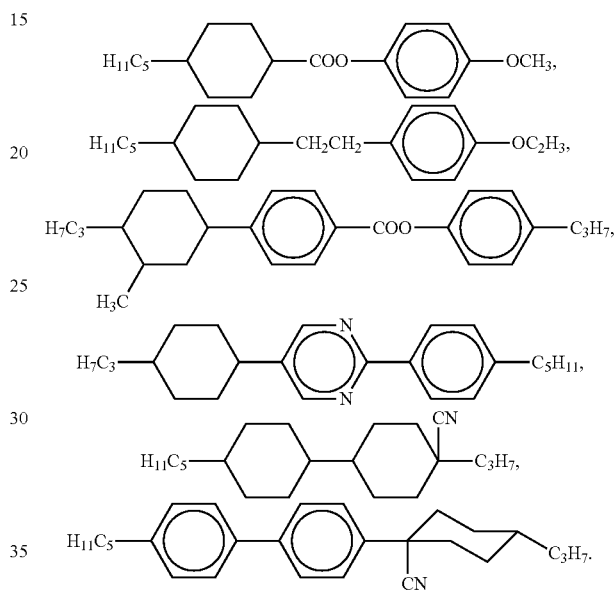

Specifically, in the liquid crystal material, a mass percentage of the liquid crystal molecules 31 is 93.0%~99.4%, a mass percentage of the reactive vertical alignment 32 material is 0.5~5.0%, a mass percentage of the polymerizable monomers 33 is 0.01%~2.0%.

Preferably, the liquid crystal material further includes photo initiator, and a mass percentage of the photo initiator is 0.1%~0.5%.

Specifically, the photo initiator includes one or a combination of more than one of azobisisobutyronitrile, dialkyl peroxide base compounds, diacyl peroxide base compounds, and lipid peroxide base compound.

Specifically, the liquid crystal molecules 31 include one or more than one of following compounds:

Specifically, the upper substrate 1 and the lower substrate 2 respectively are a TFT substrate and a CF substrate; the first electrode 12 and the second electrode 22 respectively are a pixel electrode and a common electrode.

Step 2, please refer to FIG. 2, dripping the liquid crystal material on the upper substrate 1 or the lower substrate 2, coating a sealant 4 on a peripheral position of the upper substrate 1 or the lower substrate 2, then assembling and laminating the upper substrate 1 and the lower substrate 2, and curing the sealant 4.

The reactive vertical alignment material 32 in the liquid crystal material adsorbs the upper substrate 1 and the lower substrate 2, and arranges perpendicular to the upper substrate 1 and lower substrate 2, so as to guide the liquid crystal molecules 31 arranging perpendicular to the upper substrate 1 and the lower substrate 2.

Preferably, in step 2, after the sealant 4 is coated on the peripheral position of the upper substrate 1 or the lower substrate 2, an electric conductive adhesive (not shown) is coated on a periphery of the sealant 4.

Preferably, in step 2, the upper substrate 1 and the substrate 2 are assembled and laminated in a vacuum environment.

Specifically, in step 2, curing the sealant 4 is utilized a method of heating or ultraviolet (UV) irradiation.

Figure 3:
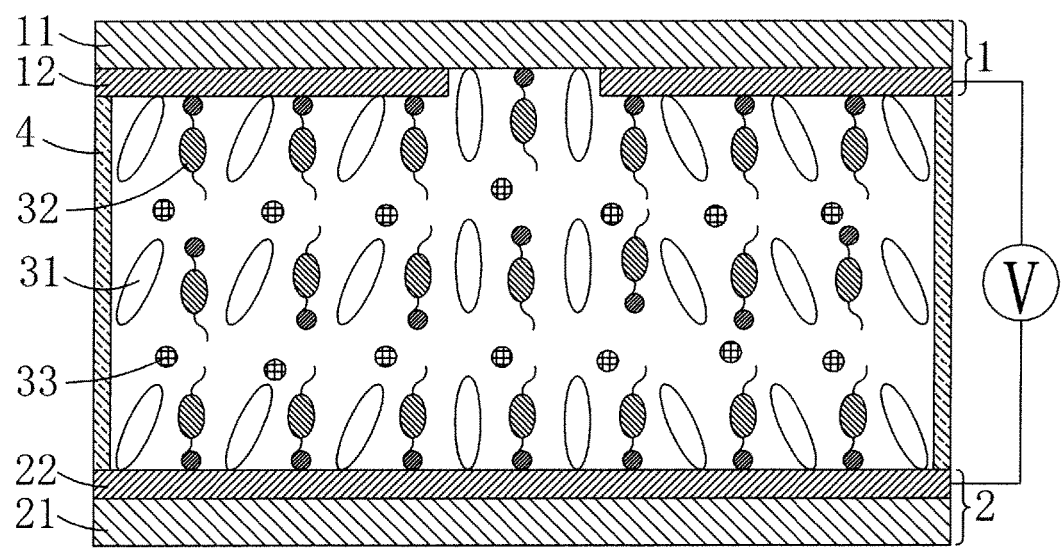
FIG. 3 is a figure schematically illustrating step 3 of the method of fabricating the liquid crystal display panel of the present application.

Step 3, as shown in FIG. 3, applying a voltage to both sides of the liquid crystal material through the first electrode 11 and the second electrode 21, to allow the liquid crystal molecules 31 occurring deflection and arranging along a direction inclined to the upper substrate 1 and the lower substrate 2.

Specifically, in step 3, the voltage applied to the both sides of the liquid crystal material is 13~25V.

Figure 4:
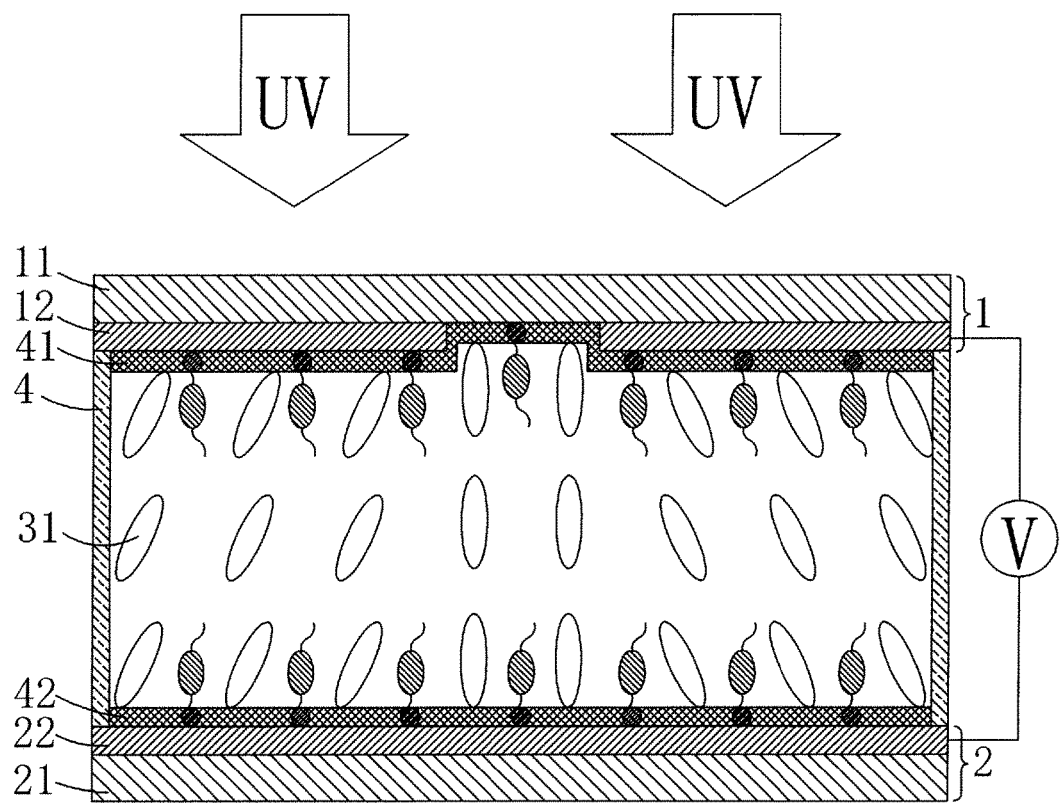
FIG. 4 is a figure schematically illustrating step 4 of the method of fabricating the liquid crystal display panel of the present application.

Step 4, as shown in FIG. 4, under the condition of applying the voltage to the liquid crystal material, irradiating ultraviolet to the liquid crystal material from a side of the upper substrate 1 or the lower substrate 2, to allow the reactive vertical alignment material 32 in the liquid crystal material occurring a polymerization with the polymerizable monomer 33 to form a polymer, wherein the polymer deposits on the upper substrate 1 toward a side of the liquid crystal material to form a first polymer film 41, and simultaneously deposits on the lower substrate 2 toward a side of the liquid crystal material to form a second polymer film 42, surfaces of both the first polymer film 41 and the second polymer film 42 have polymer projections, so as to allow the liquid crystal molecules 31 around the first polymer film 41 and the second polymer film 42 maintain the inclined direction thereof in a steric hindrance manner, after the voltage is removed.

Figure 5:
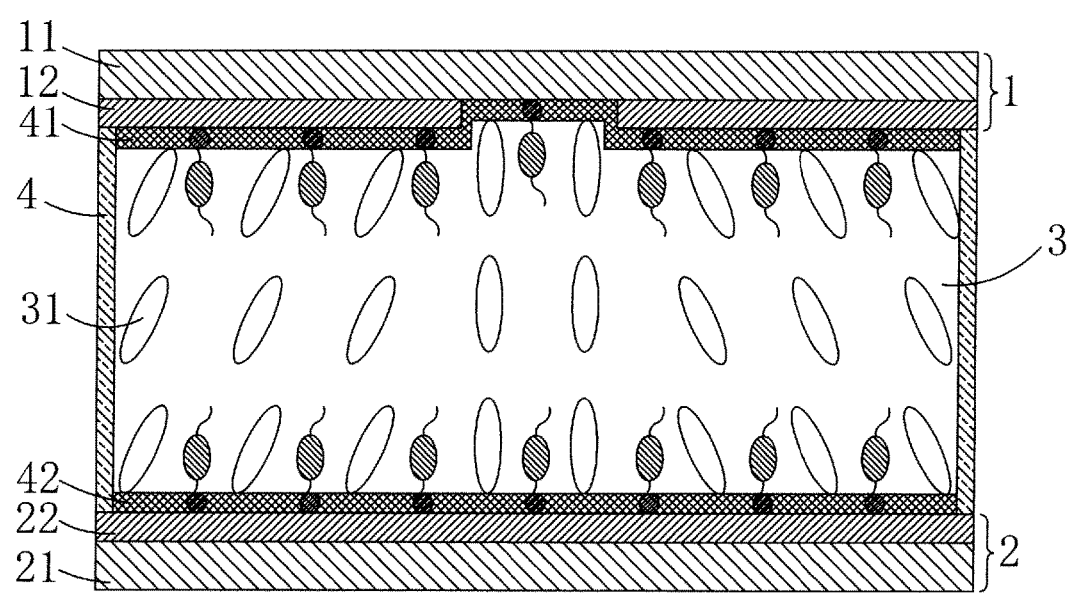
FIG. 5 is a figure schematically illustrating a structure of a liquid crystal display panel of the present application.

As shown in FIG. 5, the liquid crystal material in which the reactive vertical alignment material 32 and the polymerizable monomers 33 are removed constitutes a liquid crystal layer 3, the fabrication of the liquid crystal display panel is completed.

Specifically, in the irradiating ultraviolet of step 4, an illumination intensity of the ultraviolet is 85~100 mW/cm², an irradiation time is 20~30 min. Preferably, in step 4, ultraviolet irradiates the liquid crystal material from the side of the upper substrate (i.e. TFT substrate). Because the TFT substrate has a higher transmittance compared to the CF substrate, UV transmittance can be increased, and an effect of UV irradiation can be enhanced.

Specifically, thicknesses of the first polymer film 41 and the second polymer film 42 are 100~1200 Å. Both the first polymer film 41 and the second polymer film have polymer projections to constitute rough surfaces.

Please refer to FIG. 5, the present application further provides a liquid crystal display panel, including: oppositely disposed an upper substrate 1 and a lower substrate 2, a liquid crystal layer 3 disposed between the upper substrate 1 and the lower substrate 2, a first polymer film 41 disposed on the upper substrate 1 toward a side surface of the liquid crystal layer 3, and a second polymer film 42 disposed on the lower substrate 2 toward a side surface of the liquid crystal layer 3; wherein the upper substrate 1 includes a first substrate 11 and a first electrode 12 disposed on the first substrate 11; the lower substrate 2 includes a second substrate 21 and a second electrode 22 disposed on the second substrate 21.

The liquid crystal layer 3 includes liquid crystal molecules 31.

The surfaces of both the first polymer film 41 and the second polymer film 42 have polymer projections, which all are formed by polymerizing the polymerizable monomers 33 and the reactive vertical alignment material 32, so as to allow the liquid crystal molecules 31 in the liquid crystal layer 3 near the first polymer film 41 and the second polymer film 42 arrange along a direction inclined to the upper substrate 1 and the lower substrate 2.

A structural formula of the reactive vertical alignment material is

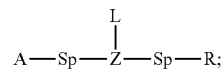

wherein A refers —OH, —COOH, —NH₂, or —NH—;

Sp refers group —(CH₂)$_n$—, or a group obtained by a —CH₂— in the group —(CH₂)$_n$— substituted with —O—, —S—, —CO—, —CO—O—, —O—CO—, —O—CO—O—, —OCH₂—, —CH₂O—, —CH═CH—, —CF═CF—, —C≡C—, —CH═CH—COO—, or —OCO—CH═CH—, wherein n is an integer 1~8;

Z refers

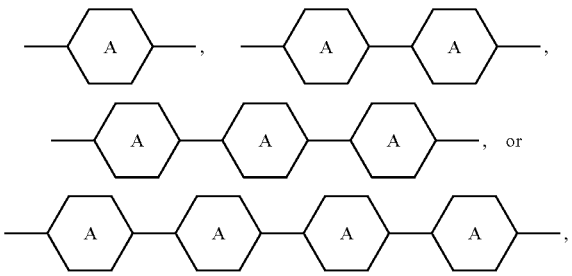

wherein

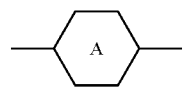

is phenyl, a group obtained by an H atom in phenyl substituted with F, Cl, Br, I, —CN, —NO₂, or —C(═O)H, or cycloalkyl;

R refers alkyl of straight chain or branched chain having 5~20 C atoms, a first group obtained by a —CH₂— in the alkyl substituted with phenyl, cycloalkyl, —CONH—, —COO—, —O—CO—, —S—, —CO—, or —CH═CH—, a second group obtained by an H atom in the alkyl substituted with F or Cl atom, or a third group obtained by an H atom in the first group substituted with F or Cl atom;

L refers a polymerizable group connecting to group Z, and includes any one, an two, or any three of following three groups:

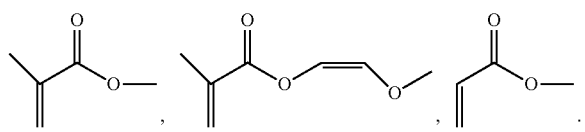

Specifically, the reactive vertical alignment material 32 includes one or to more than one of following compounds:

29
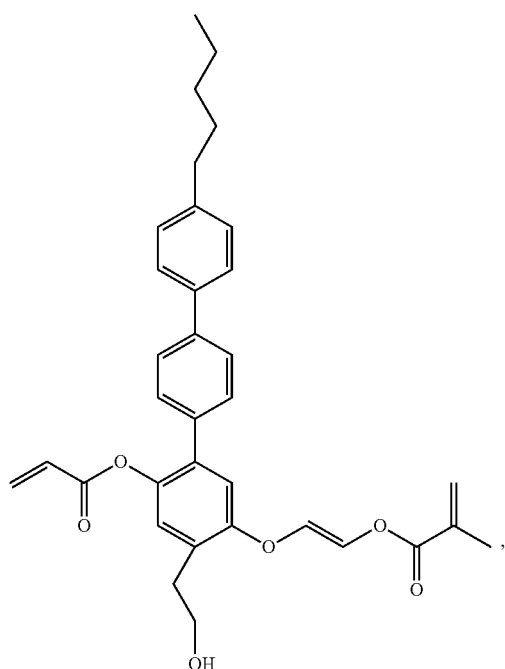
30
-continued
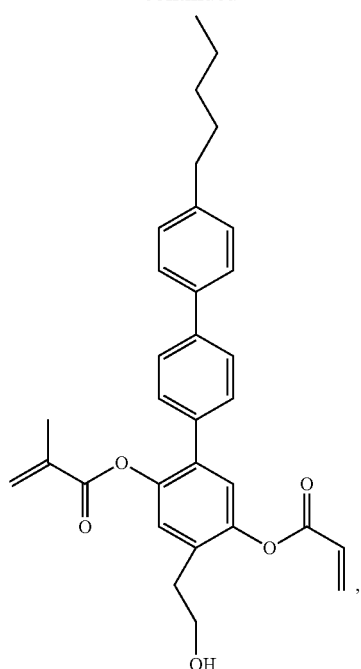
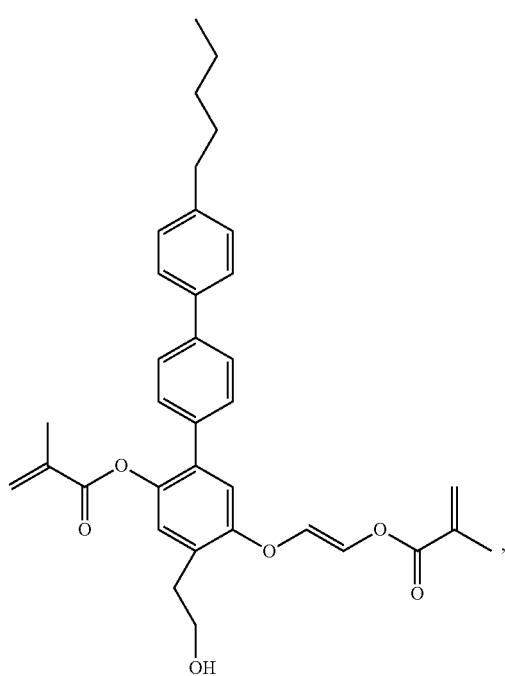
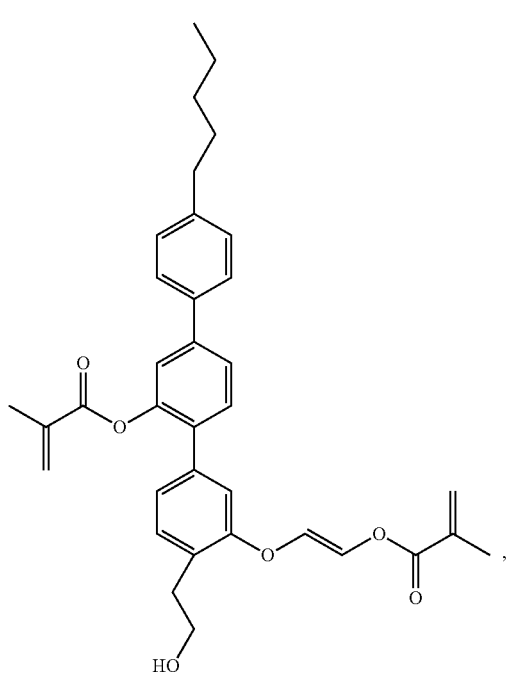

-continued

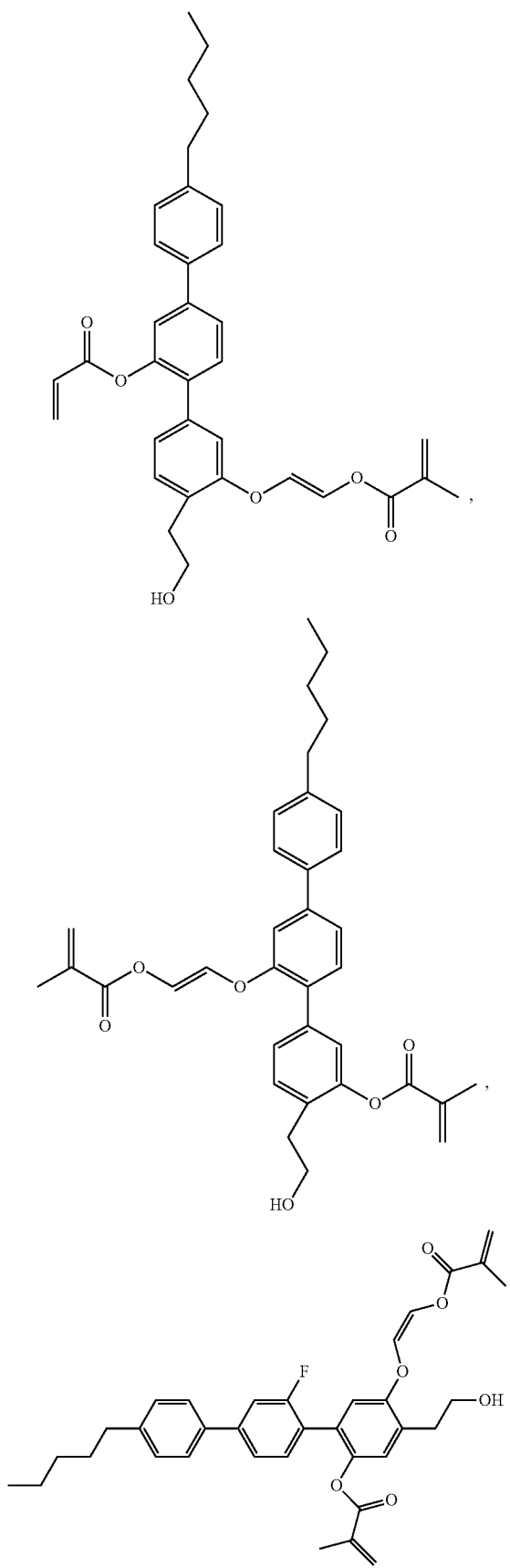

Specifically, the thicknesses of the first polymer film 41 and the second polymer film 42 are 100~1200 Å. Both the first polymer film 41 and the second polymer film have polymer projections to constitute rough surfaces.

Specifically, the polymerizable monomers 33 include one or a combination of more than one of acrylates, acrylate derivatives, methacrylates, methacrylate derivatives, styrene, styrene derivatives, and epoxy resin; wherein the epoxy resin can be fatty amine base epoxy resins.

Specifically, the liquid crystal molecules 31 include one or more than one of following compounds:

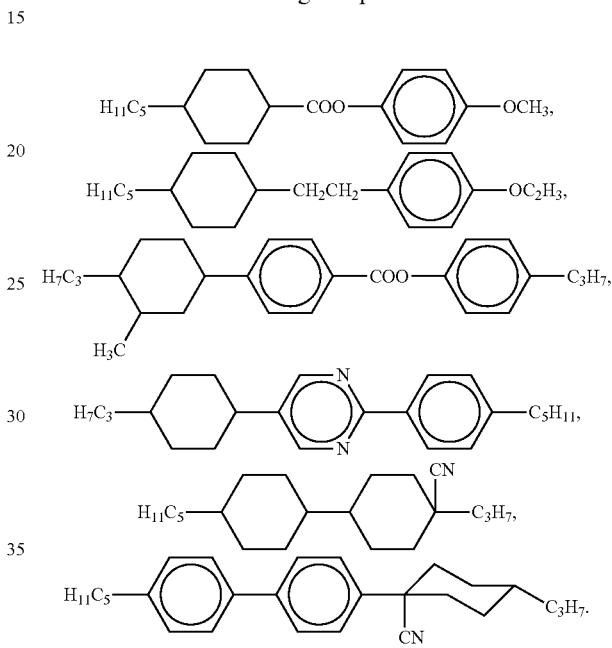

Specifically, the liquid crystal display panel further includes a sealant 4 disposed between the upper substrate 1 and the lower substrate 2 and located at periphery of the liquid crystal layer 3. Preferably, the liquid crystal display panel further includes an electric conductive adhesive (not shown) is located at a periphery of the sealant 4.

Specifically, the upper substrate 1 and the lower substrate respectively are a TFT substrate and a CF substrate; the first electrode 12 and the second electrode respectively are a pixel electrode and a common electrode.

The reactive vertical alignment material 32 will be described in a method of fabricating a specific compound in an embodiment as follows.

Step 1 (compound a→compound b): adding 20.0 g compound a (67.6 mmol) into 600 mL tetrahydrofuran (THF), and cooling down to −78° C.; then, dropping 50 mL hexane containing N-butyllithium of 75 mmol; stirring for 10 min; then, adding 40 mL THF containing 4 g ethylene oxide (the system temperature is 2° C.); then, adding 10 mL trifluoroethylester at temperature of −78° C., and stirring for 15 min, to obtain 11 g compound b after separation and purification.

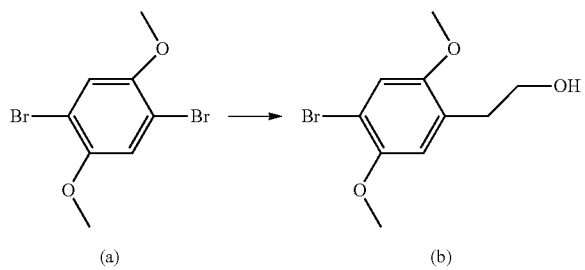

(a) → (b)

Step 2 (compound b+compound c→compound d): dissolving 20 mmol compound b and 20 mmol compound c in 200 mL toluene, and adding 100 mL ethanol and 40 mL 1 mol/L Na$_2$CO$_3$; after purging argon for 30 min, adding 100 mg tetrakis(triphenylphosphine)palladium, heating and refluxing for 60 min, to obtain product d after separation and extraction.

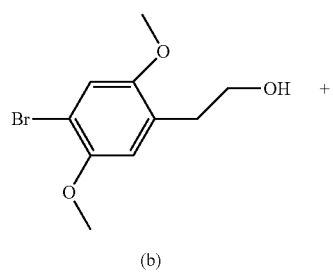

(b) +

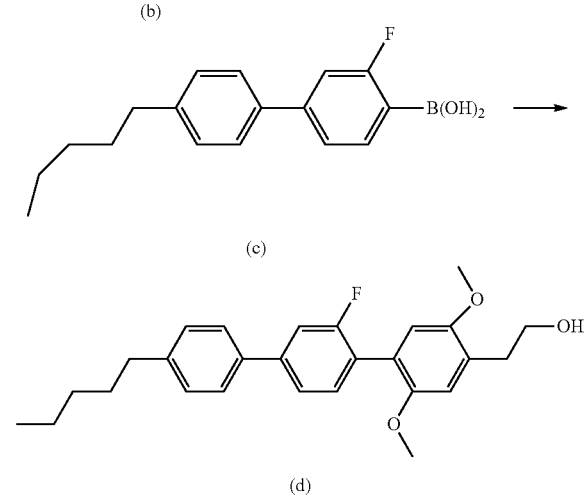

(c)

(d)

Step 3 (compound d→compound e): dissolving 10 mmol compound d in 50 mL dichloromethane, and cooling down to −28° C.; then, adding 20 mol boron trifluoride, stirring for 3 hours at a condition of −25° C.; after that, adding mol/L NaOH at a condition of ice bath, to obtain compound e after separation and purification.

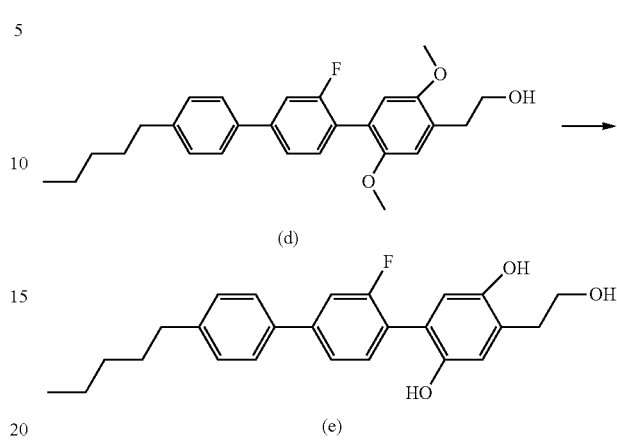

(d)

(e)

Step 4(compound e→compound f): dissolving 3 mmol compound e and 3.5 mmol imidazole in 3 mL trifluoroacetic acid (THF), and cooling down to 2° C.; then, gradually dropping THF solution (4 mL) containing tert-butyldimethylsilyl chloride (3.5 mmol), (a dropping time is 30 min); then, after stirring for 60 min at room temperature, adding ammonium chloride solution, and extracting a product with methyl tert-butyl ether, to obtain compound f after purification.

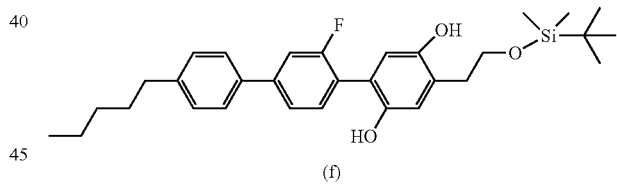

(e)

(f)

Step 5 (compound f→compound g): dissolving 10 mmol compound f, mmol tetrabutylammonium bromide, 12 mmol potassium carbonate, and mmol 2-bromo-1,1-diethoxyethane in 20 mL dimethylformamide (DMF), heating and refluxing for 3 hours; after cooling, adding 10 mL water, extracting with 5 mL toluene for 3 times, to obtain compound g after separation and purification.

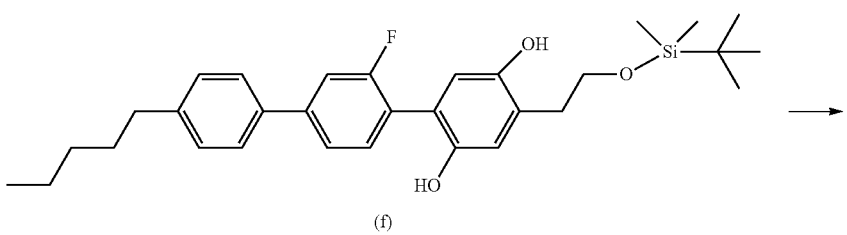

(f)

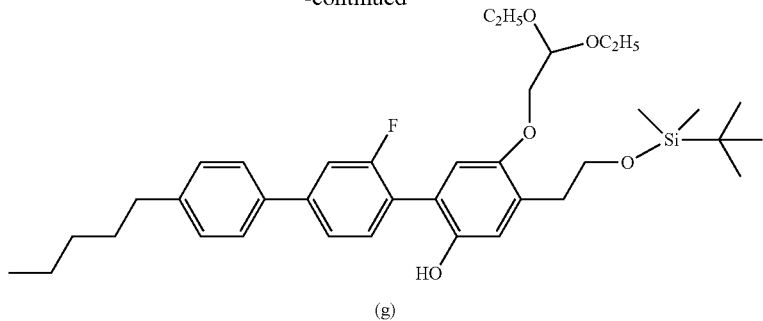

(g)

Step 6 (compound g→compound h): dissolving 4 mmol compound g, mmol methacrylate, and 0.2 mmol 4-(dimethylamino) pyridine in 25 mL dichloromethane, and cooling the mixture system down to 1° C.; then, gradually dropping dichloromethane containing carbodiimide (6 mmol), maintaining the system at a temperature 1~4° C. during dropping; finally, stirring and reacting for 18 h at room temperature, to obtain compound h after separation and extraction.

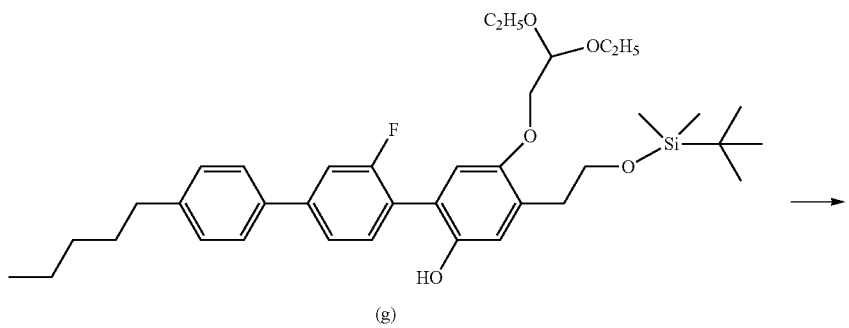

(g)

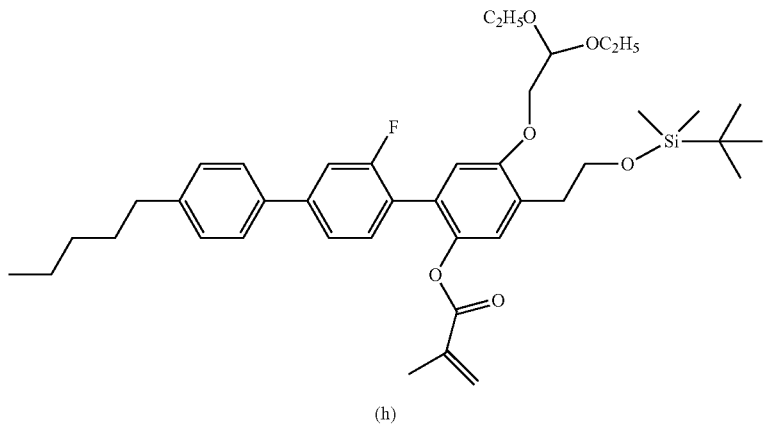

(h)

Step 7 (compound h→compound i): dissolving 10 mmol compound h in 40 mL chloroform, dropping 60 mmol trifluoroacetic acid at room temperature; after reacting for 16 h, adding 100 mL NaHCO₃ solution (containing 60 mmol NaHCO₃); then, extracting with 500 mL ethyl acetate for 3 times; dissolving and washing by using NaCl solution of 3% mass fraction for 3 times, to obtain compound i.

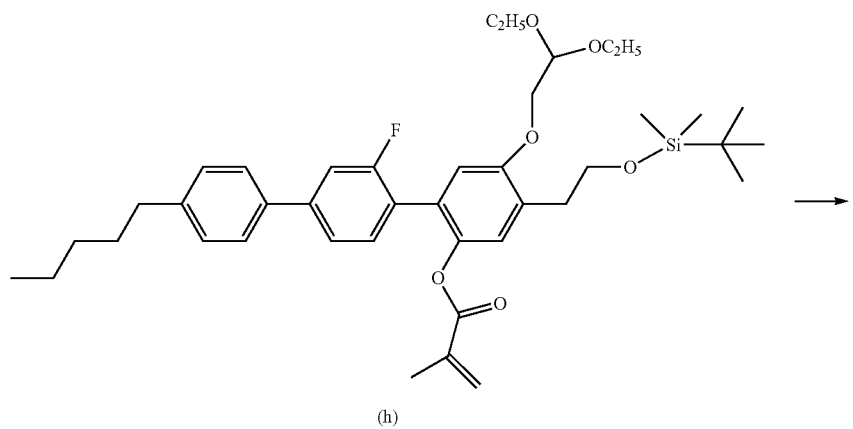
(h)
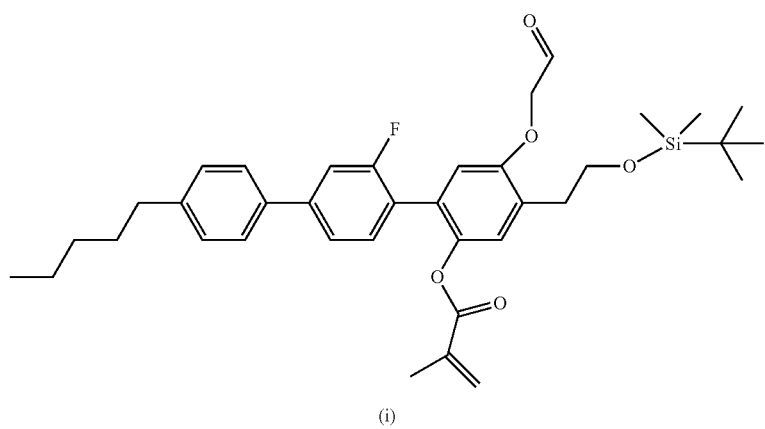
(i)
Step 8 (compound I→compound j): dissolving 10 mmol compound I in 10 mL toluene, sequentially adding 50 mmol methacrylic anhydride, 2 mol potassium carbonate, and 1 mL DMF, heating and refluxing for 20 h; then, cooling down, to obtain compound j after separation and purification.
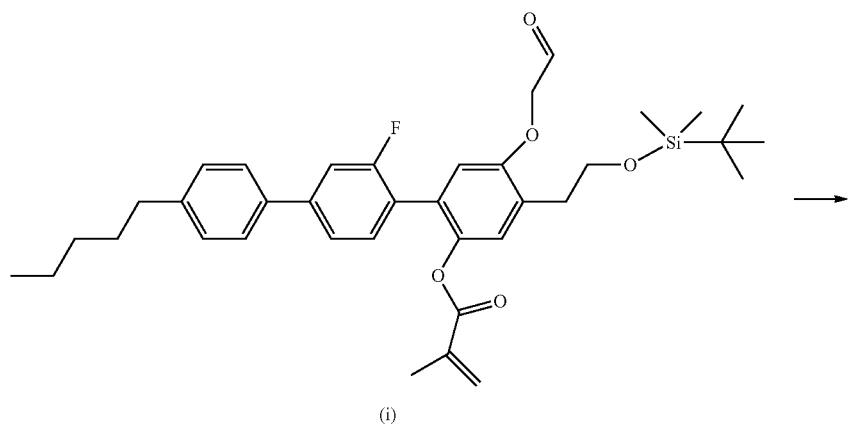
(i)

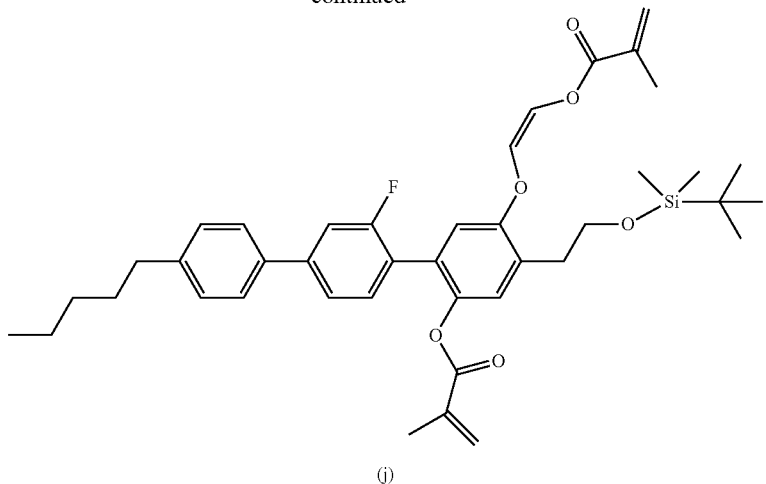
(j)
Step 9 (compound j→compound k): dissolving 2.5 mmol compound j in 50 mL THF (the system temperature is 2° C.); gradually dropping 2 mL hydrochloride acid of 2 mol/L concentration, and gradually returning to room temperature; reacting for 3 h, to obtain compound k after espration and purification.
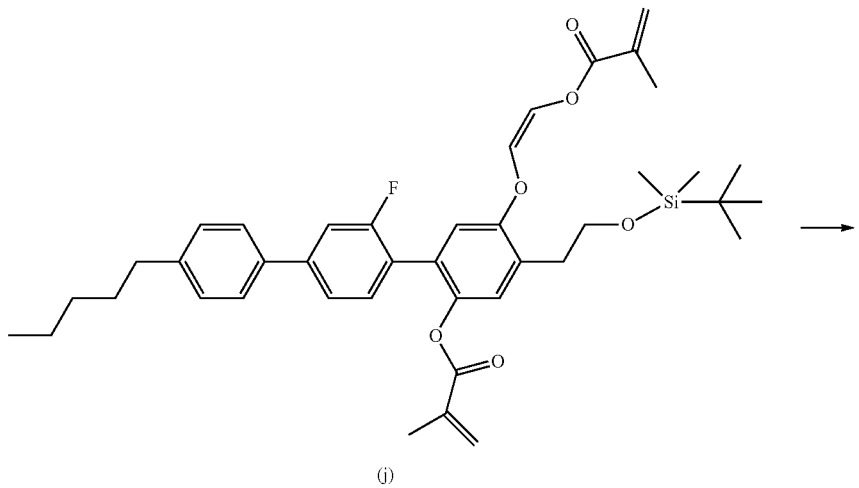
(j)
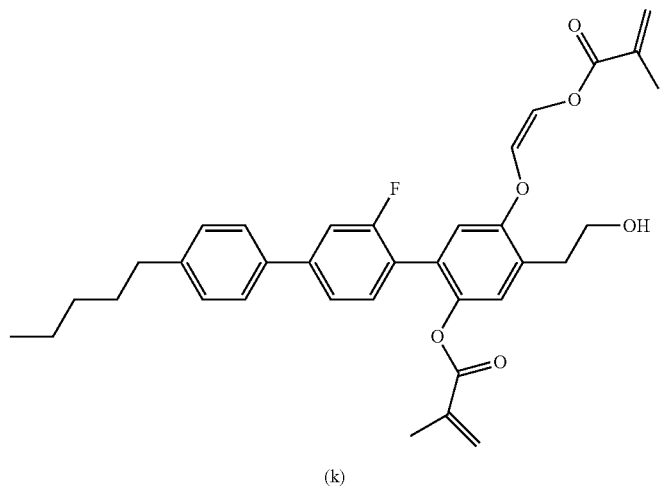
(k)

H[1]-NMR data of compound k is as follows: δ: 0.96 (3H), 1.33 (2H), 1.29 (2H), 1.62 (2H), 2.55 (2H), 7.18 (2H), 7.43 (2H), 7.25 (1H), 7.31 (1H), 7.52 (1H), 6.87 (1H), 6.82 (1H), 6.01 (1H), 6.54 (1H), 1.93 (6H), 6.27 (1H), 5.72 (1H) 5.49 (1H), 5.98 (1H), 2.74 (2H), 3.86 (2H), 2.0 (1H).

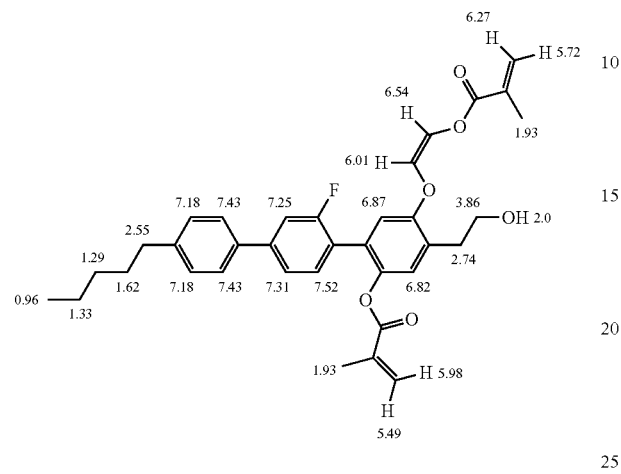

In summary, the present application provides a liquid crystal material, a method of fabricating a liquid crystal display panel, and a liquid crystal display panel. The liquid crystal material of the present application includes liquid crystal molecules, polymerizable monomers and a reactive vertical alignment material, the polymerizable monomers and the reactive vertical alignment to material can occur a polymerization under ultraviolet irradiation to form a polymer, while the polymer deposits on a substrate to form a polymer film capable of replacing the PI alignment film, the reactive vertical alignment material includes a polymerizable group L that strengthens polymerization ability of the reactive vertical alignment material, increases compactness of forming the polymer film, improves morphology of the polymer film, and enhances panel quality. The method of fabricating the liquid crystal display panel of the present application eliminates the fabricating process of the PI alignment film, the method has simple process and low cost. The liquid crystal display panel utilizes the polymer film, which is obtained by polymerizing the polymerizable monomers and the reactive vertical alignment material, to replace the PI alignment film, that not only meets the aspect of liquid crystal alignment, but also prevent impurities in the CF substrate to diffuse into the liquid crystal layer, so as to greatly enhance quality of the panel, and to have a low fabricating cost.

Based on the above description, an ordinarily skilled in the art can complete various similar modifications and arrangements according to the technical programs and ideas of the present application, and the scope of the appended claims of the present application should encompass all such modifications and arrangements.

What is claimed is:

1. A liquid crystal material, comprising liquid crystal molecules, a reactive vertical alignment material, and polymerizable monomers;

the reactive vertical alignment material comprising at least one of following compounds:

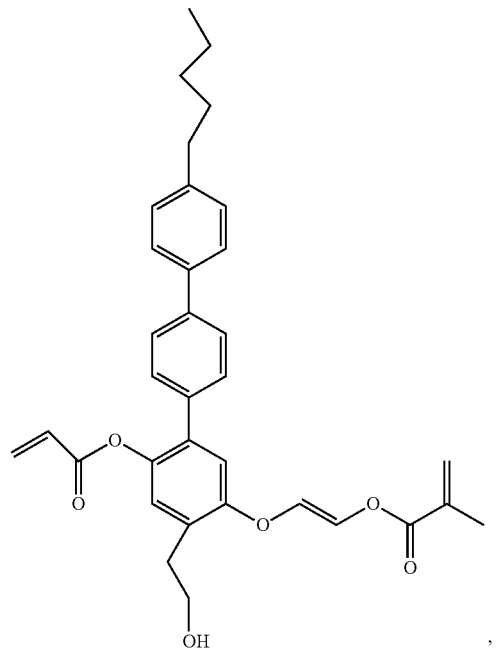

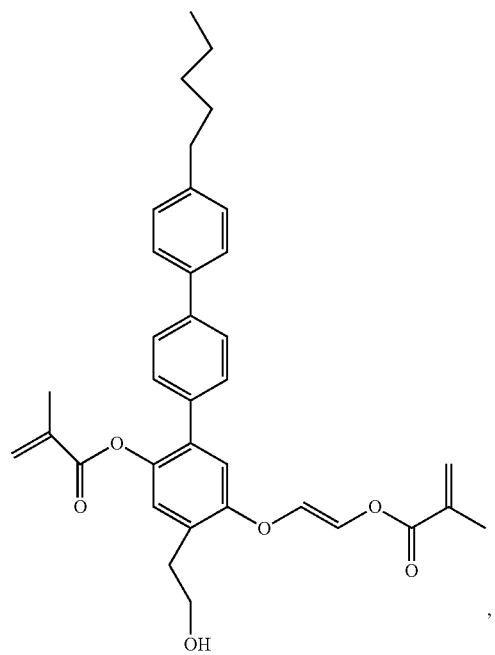

43
-continued
44
-continued
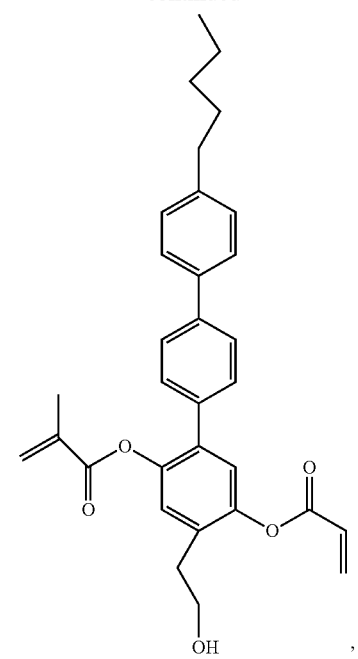
,
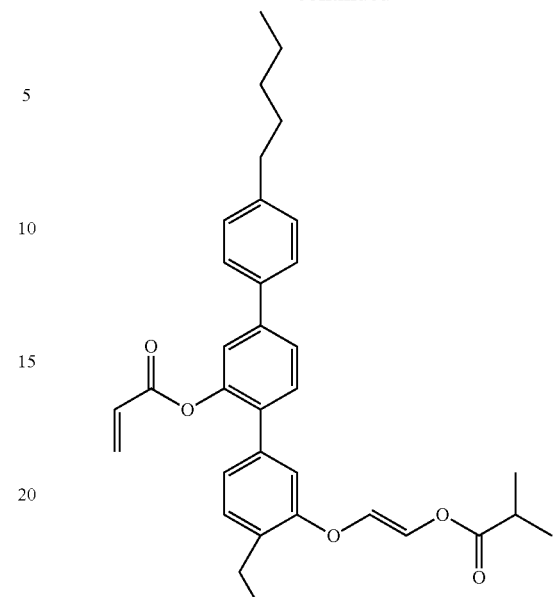
,
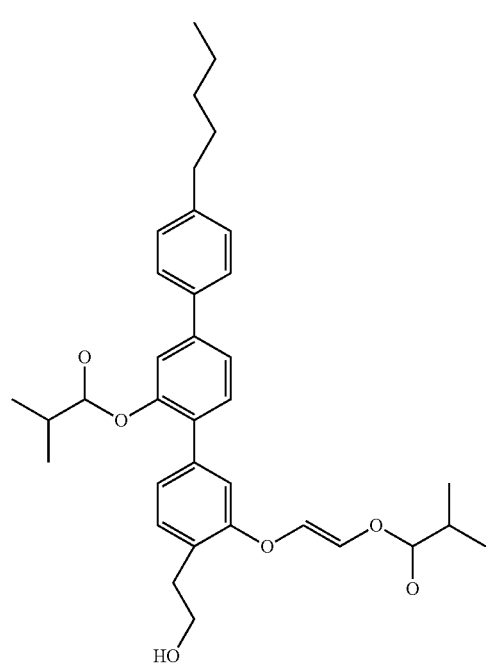
,
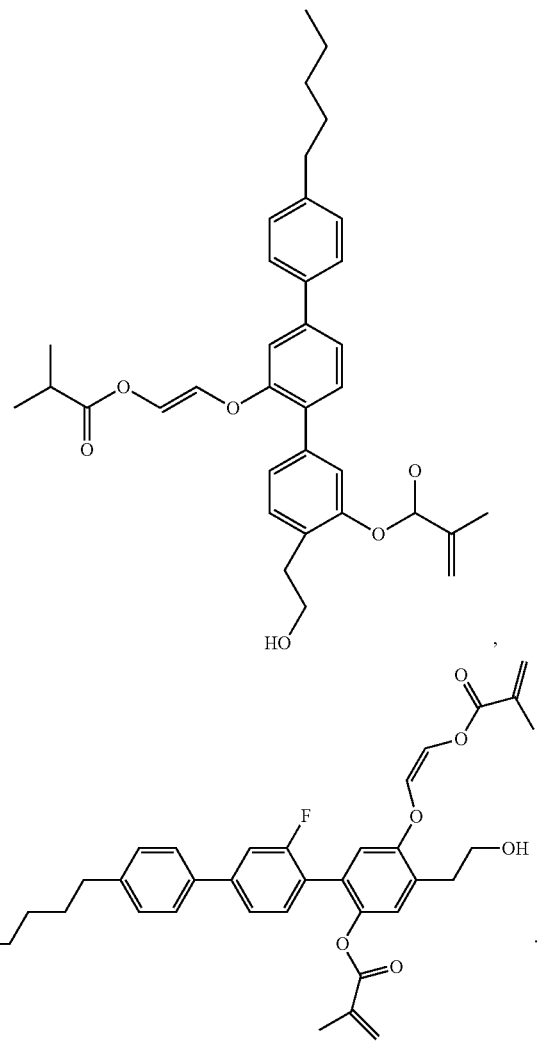
,

2. The liquid crystal material according to claim 1, wherein a mass percentage of the liquid crystal molecules is 93.0%~99.4%, a mass percentage of the reactive vertical alignment material is 0.5%~5.0%, a mass percentage of the polymerizable monomers is 0.01%~2.0%;

the polymerizable monomers comprise one or a combination of more than one of acrylates, acrylate derivatives, methacrylates, methacrylate derivatives, styrene, styrene derivatives, and epoxy resin.

3. A method of fabricating a liquid crystal display panel, comprising following steps:

step 1, providing an upper substrate, a lower substrate, and a liquid crystal material; the upper substrate comprising a first substrate, and a first electrode disposed on the first substrate; the lower substrate comprising a second substrate, and a second electrode disposed on the second substrate;

the liquid crystal material comprising liquid crystal molecules, a reactive vertical alignment material, and polymerizable monomers;

the reactive vertical alignment material comprising at least one of following compounds:

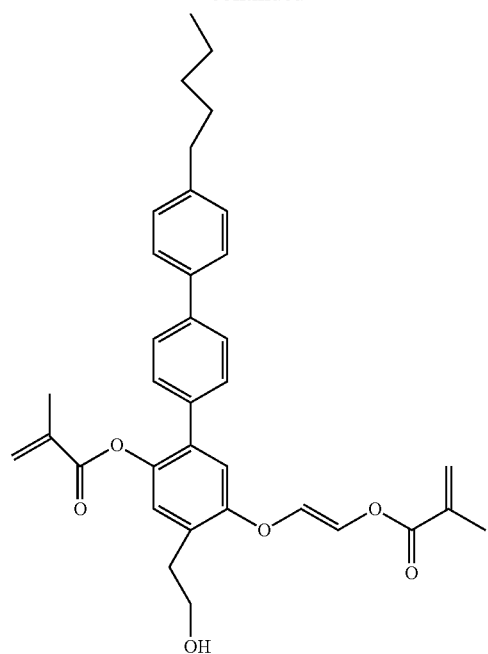

-continued

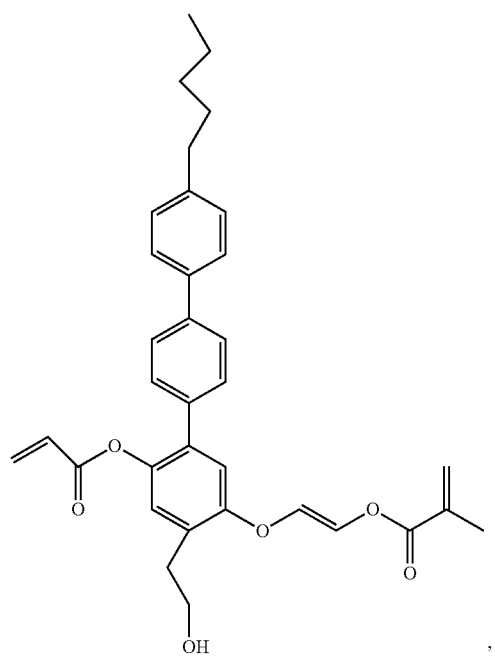

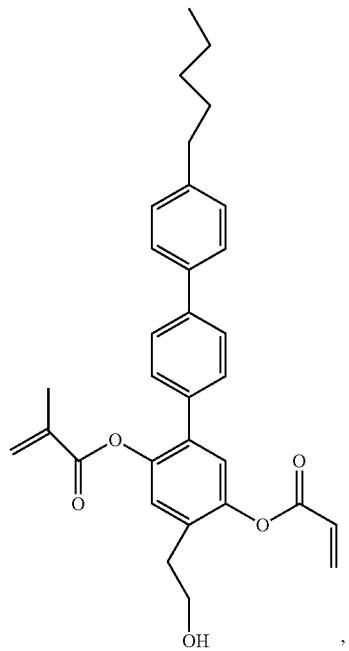

-continued

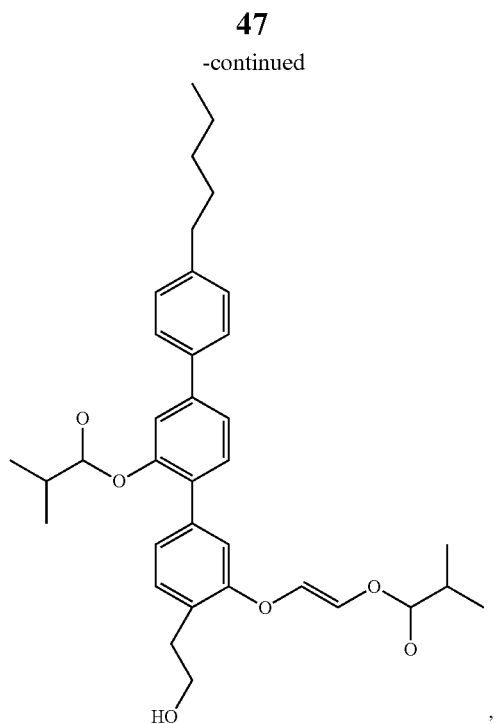

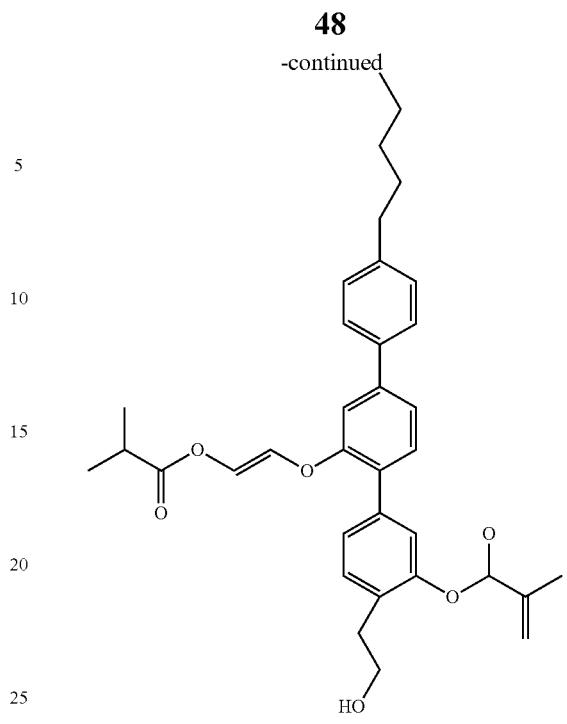

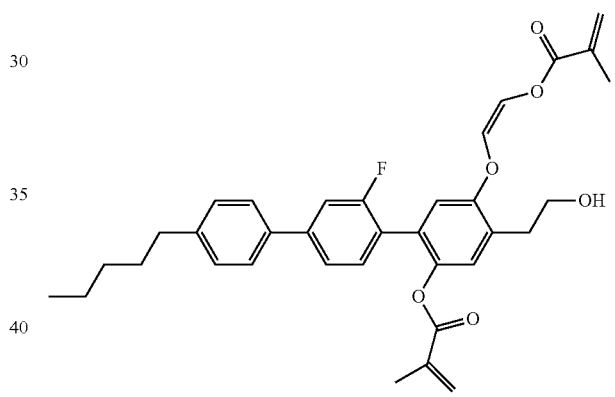

step 2, dripping the liquid crystal material on the upper substrate or the lower substrate, coating a sealant on a peripheral position of the upper substrate or the lower substrate, then assembling and laminating the upper substrate and the lower substrate, and curing the sealant;

the reactive vertical alignment material in the liquid crystal material adsorbs the upper substrate and the lower substrate, and arranges perpendicular to the upper substrate and the lower substrate, so as to guide the liquid crystal molecules arranging perpendicular to the upper substrate and the lower substrate;

step 3, applying a voltage to both sides of the liquid crystal material through the first electrode and the second electrode, to allow the liquid crystal molecules occurring deflection and arranging along a direction inclined to the upper substrate and the lower substrate;

step 4, under the condition of applying the voltage to the liquid crystal material, irradiating ultraviolet to the liquid crystal material from a side of the upper substrate or the lower substrate, to allow the reactive vertical alignment material in the liquid crystal material occurring a polymerization with the polymerizable monomer to form a polymer, wherein the polymer deposits on the upper substrate toward a side of the liquid crystal material to form a first polymer film, and simultaneously deposits on the lower substrate toward a side of the liquid crystal material to form a second polymer film, surfaces of both the first polymer film and the second polymer film have polymer projections, so as to allow the liquid crystal molecules near the first polymer film and the second polymer film maintain the inclined direction thereof in a steric hindrance manner, after the voltage is removed;

constituting a liquid crystal layer by the liquid crystal material in which the reactive vertical alignment material and the polymerizable monomers are removed, to complete the fabrication of the liquid crystal display panel.

4. The method of fabricating the liquid crystal display panel according to claim/r, a mass percentage of the liquid crystal molecules is 93.0%~99.4%, a mass percentage of the reactive vertical alignment material is 0.5%~5.0%, a mass percentage of the polymerizable monomers is 0.01%~2.0%;

the polymerizable monomers comprise one or a combination of more than one of acrylates, acrylate derivatives, methacrylates, methacrylate derivatives, styrene, styrene derivatives, and epoxy resin.

5. The method of fabricating the liquid crystal display panel according to claim 3, wherein, in step 3, the voltage applied to the both sides of the liquid crystal material is 13~25V; in the irradiating ultraviolet of step 4, an illumination intensity of the ultraviolet is 85~100 mW/cm², an irradiation time is 20~30 min, thicknesses of the first polymer film and the second polymer film are 100~1200 Å.

6. A liquid crystal display panel, comprising: oppositely disposed an upper substrate and a lower substrate, a liquid crystal layer disposed between the upper substrate and the lower substrate, a first polymer film disposed on the upper substrate toward a side surface of the liquid crystal layer, and a second polymer film disposed on the lower substrate toward a side surface of the liquid crystal layer; wherein the upper substrate comprises a first substrate and a first electrode disposed on the first substrate; the lower substrate comprises a second substrate and a second electrode disposed on the second substrate;

the liquid crystal layer comprises liquid crystal molecules;

both the first polymer film and the second polymer film are formed by polymerizing the polymerizable monomer and the reactive vertical alignment material, and surfaces of both the first polymer film and the second polymer film have polymer projections, so as to allow the liquid crystal molecules near the first polymer film and the second polymer film arrange along a direction inclined to the upper substrate and the lower substrate;

the reactive vertical alignment material comprises at least one of following compounds:

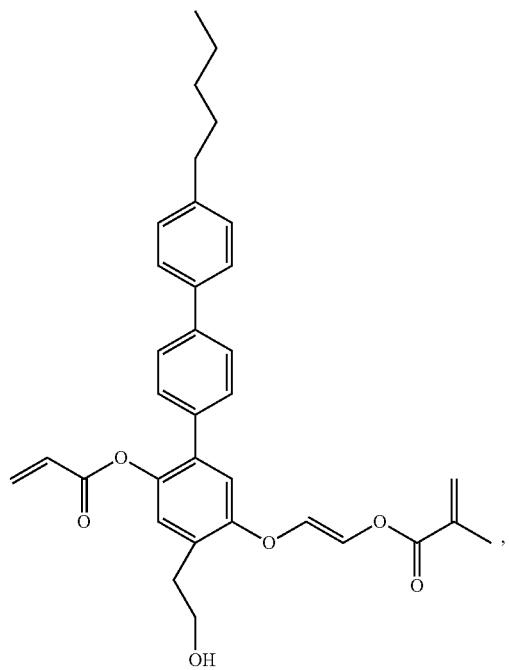

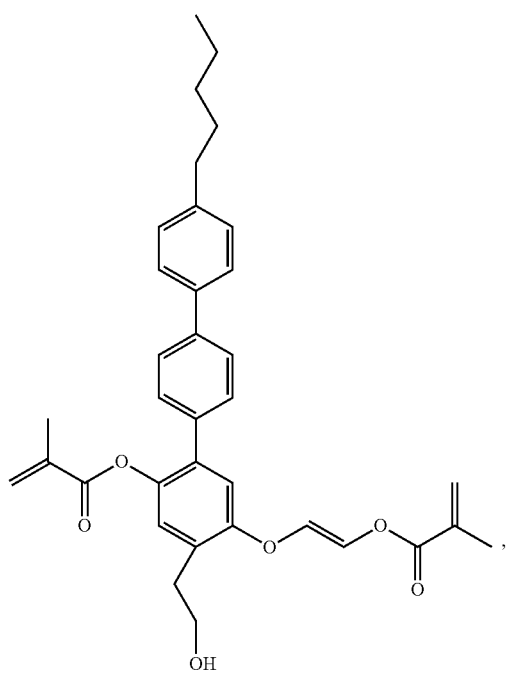

51
-continued
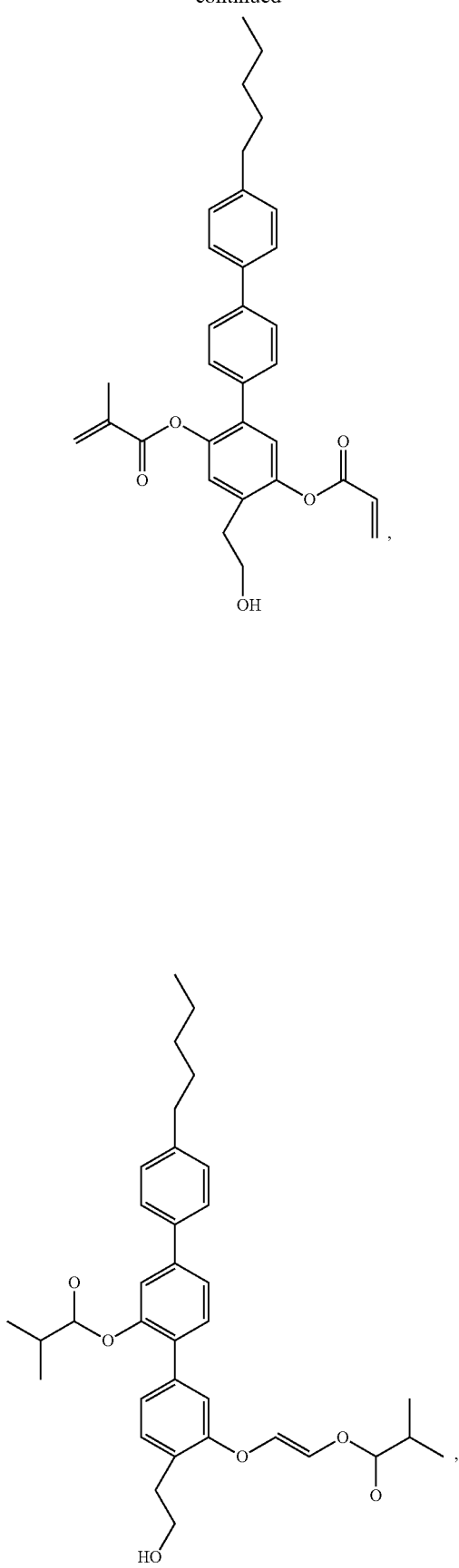
52
-continued
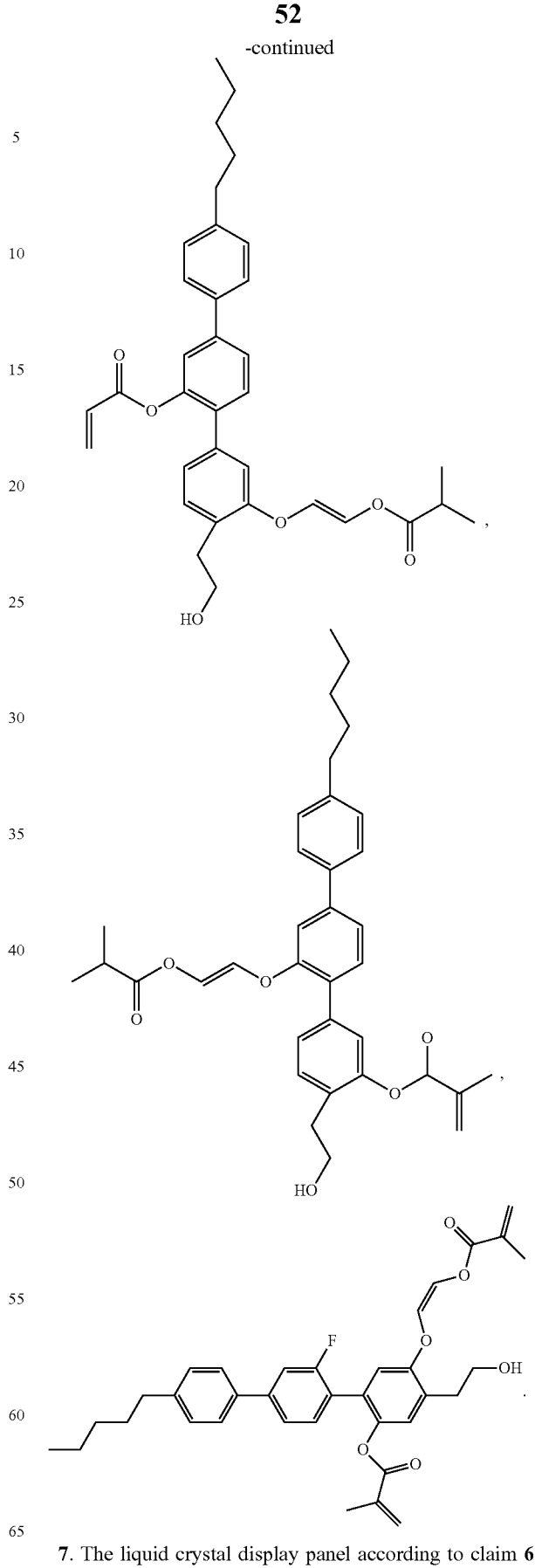
7. The liquid crystal display panel according to claim 6, wherein the polymerizable monomers comprise one or a combination of more than one of acrylates, acrylate derivatives, methacrylates, methacrylate derivatives, styrene, styrene derivatives, and epoxy resin; thicknesses of the first polymer film and the second polymer film are 100~1200 Å.

* * * * *